(12) United States Patent
Puybasset et al.

(10) Patent No.: US 10,176,578 B2
(45) Date of Patent: Jan. 8, 2019

(54) METHOD FOR QUANTIFYING BRAIN INJURIES

(71) Applicant: ASSISTANCE PUBLIQUE—HOPITAUX DE PARIS, Paris (FR)

(72) Inventors: Louis Puybasset, Paris (FR); Damien Galanaud, Paris (FR); Habib Benali, Gennevieve des Bois (FR); Vincent Perlbarg, Paris (FR); Stephane Lehericy, Paris (FR)

(73) Assignee: ASSISTANCE PUBLIQUE—HOPITAUX DE PARIS, Paris (FR)

( * ) Notice: Subject to any disclaimer, the term of this patent is extended or adjusted under 35 U.S.C. 154(b) by 460 days.

(21) Appl. No.: 14/436,379

(22) PCT Filed: Oct. 15, 2013

(86) PCT No.: PCT/FR2013/052454
§ 371 (c)(1),
(2) Date: Sep. 14, 2015

(87) PCT Pub. No.: WO2014/060695
PCT Pub. Date: Apr. 24, 2014

(65) Prior Publication Data
US 2015/0379713 A1    Dec. 31, 2015

(30) Foreign Application Priority Data

Oct. 17, 2012   (FR) ...................................... 12 59910
Feb. 7, 2013    (FR) ...................................... 13 51046
Feb. 7, 2013    (FR) ...................................... 13 51047

(51) Int. Cl.
G06K 9/00      (2006.01)
G06T 7/00      (2017.01)
(Continued)

(52) U.S. Cl.
CPC .......... G06T 7/0014 (2013.01); A61B 5/0042 (2013.01); A61B 5/055 (2013.01);
(Continued)

(58) Field of Classification Search
CPC ..... A61B 5/055; A61B 5/4064; A61B 5/0042; A61B 2576/026; A61B 5/7275;
(Continued)

(56) References Cited

U.S. PATENT DOCUMENTS 8,742,754 B2 *  6/2014  Hasan .................... A61B 5/055
                                                        324/307
9,494,669 B2 * 11/2016  Song ................. G01R 33/56341
(Continued)

OTHER PUBLICATIONS

A. Sidaros et al. "Diffusition tensor imaging during recovery from severe traumatic brain injury and relation to clinical outcome: a longitudinal study"; Feb. 2008; vol. 131; No. 2.
(Continued)

*Primary Examiner* — Tom Y Lu
(74) *Attorney, Agent, or Firm* — Cantor Colburn LLP

(57) ABSTRACT

The invention relates to an ex vivo method for detecting and/or quantifying brain injuries. The invention also relates to an ex vivo method for monitoring the evolution of a brain injury, and to an ex vivo method for predicting when a patient will come out of a coma. The invention is particularly applicable in the field of medicine and in the field of clinical studies.

10 Claims, 11 Drawing Sheets

< left – right > radiological convention

(51) Int. Cl.
A61B 5/00 (2006.01)
A61B 5/055 (2006.01)
G01R 33/563 (2006.01)
G06K 9/46 (2006.01)
G06K 9/52 (2006.01)
G06K 9/62 (2006.01)
G06T 7/238 (2017.01)

(52) U.S. Cl.
CPC .......... A61B 5/4064 (2013.01); A61B 5/7264 (2013.01); A61B 5/7267 (2013.01); A61B 5/7275 (2013.01); G01R 33/56341 (2013.01); G06K 9/46 (2013.01); G06K 9/52 (2013.01); G06K 9/6215 (2013.01); G06K 9/6267 (2013.01); G06T 7/0012 (2013.01); G06T 7/238 (2017.01); A61B 5/4842 (2013.01); A61B 2576/026 (2013.01); G06K 2009/4666 (2013.01); G06T 2207/10088 (2013.01); G06T 2207/30016 (2013.01)

(58) Field of Classification Search
CPC ... A61B 5/7267; A61B 5/4842; A61B 5/7264; A61B 10/0041; A61B 10/0241; A61B 2010/045; A61B 2576/023; A61B 5/0044; A61B 5/201; A61B 5/202; A61B 5/4041; A61B 5/425; A61B 5/431
See application file for complete search history.

(56) References Cited

U.S. PATENT DOCUMENTS

2011/0218253 A1* 9/2011 Lange ............... A61K 45/00 514/789
2013/0245422 A1* 9/2013 D'Arcy ............. A61B 5/0484 600/409

OTHER PUBLICATIONS

Margaret Oni et al. "Diffusion tensor Imaging analysis of frontal lobes in pediatric traumatic brain injury" Journal of child neurology; Aug. 1, 2010; vol. 25; No. 8; pp. 976-984.
International Search Report dated Apr. 24, 2014 re: Application No. PCT/FR2013/052454.
Joshua Betz et al. "Prognostic Value of Diffusion Tensor Imaging Parameters in Severe Traumatic Brain Injury" Journal of Neurotrauma, Apr. 17, 2012, vol. 29, No. 7, pp. 1292-1305, XP050076969.
K C Chan et al. "Late measures of microstructural alterations in severe neonatal hypoxic-ischemic encephalopathy by MR diffusion tensor imaging", International Journal of Developmental Neuroscience, Oct. 1, 2009, vol. 27, No. 6, pp. 607-615, XP026469807.
Karen Caeyenberghs et al. "Brain-behavior relationships in young traumatic brain injury patients: DTI metrics are highly correlated with postural control" Human Brain Mapping; Jul. 8, 2010; vol. 31, No. 7, pp. 992-1002, XP055069954.
Margaret B. Oni et al. "Diffusion Tensor Imaging Analysis of Frontal Lobes in Pediatric Traumatic Brain Injury" Journal of Child Neurology, Decker Periodicals, Aug. 1, 2010, vol. 25, No. 8, pp. 976-984 XP008168487.
Miia Pitkonen et al. "Long-term evolution of diffusion tensor indices after temporary experimental ischemic stroke in rats", Brain Research, Elsevier, Jan. 19, 2012, vol. 1445, No. 19, pp. 103-110 XP028467880.
N S Metwalli et al. "Utility of axial and radial diffusivity from diffusion tensor MRI as markers of neurodegeneration in amyotrophic lateral sclerosis", Brain Research, Elsevier, Aug. 12, 2010, vol. 1348, pp. 156-164, XP027117429S.
S. Wang et al. "Mild Hypoxic-Ischemic Injury in the Neonatal Rat Brain: Longitudinal Evaluation of White Matter Using Diffusion Tensor MR Imaging", AJNR, American Journal of Neuroradiology, Nov. 1, 2009, vol. 30, No. 10, pp. 1907-1913, XP055069764.
Vincent Perlbarg et al. "Relation between brain lesion location and clinical outcome in patients with severe traumatic brain injury: A diffusion tensor imaging study using voxel-based approaches", Human Brain Mapping, Jun. 8, 2009, vol. 30, No. 12, pp. 3.
Basser et al. "MR diffusion tensor spectroscopy and imaging"; Biophysical Journal; 1994; vol. 66 No. 1; pp. 259-267.
C. Rorden et al. "Stereotaxic display of brain lesions" Behavioral Neurology; 2000 vol. 12; pp. 191-2000.
Chih-Chung Chang et al. "LIBSVM: a library for support vector machines" ACM Transactions on Intelligent Systems and Technology; 2:27:1-27:27; 2011; http://www.csie.ntu.edu.tw/~cjlin/libsvm. http://www.csie.ntu.edu.tw/~cjlin/libsvmtools/#feature_selection_tool.
J.L.R. Andersson et al. "Non-linear registration, aka Spatial normalisation" FMRIB Technical Report TR07JA1; 2007 www.fmrib.ox.ac.uk/analysis/techrep; 2007.
J.L.R. Andersson et al. "Non-linear registration, aka Spatial normalisation" FMRIB Technical Report TR07JA2; www.fmrib.ox.ac.uk/analysis/techrep; 2007.
J.T. Giacino et al. "Outcome after severe traumatic brain injury: coma, the vegetative state, and the minimally responsive state" J Head Trauma Rehabil; vol. 10; pp. 40-56.
M. Jenkinson et al. "A global optimisation method for robust affine registration of brain images" Medical Image Analysis 2001; vol. 5, No. 2; pp. 143-156.
M. Jenkinson et al. "Improved optimisation for the robust and accurate linear registration and motion correction of brain images", NeuroImage; 2002; vol. 17, No. 2; pp. 825-841.
P. J. Basser et al. "Microstructural and Physiological Features of Tissues Elucidated" by Quantitative-Diffusion-Tensor MRI. Journal of Magnetic Resonance, 1996, vol. 111 No. 3; pp. 209-219.
R. Picard et al. "Cross-Validation of Regression Models" Journal of the American Statistical Association; 1984; vol. 79; vol. 387; pp. 575-583.
Robert W. Cox, et al. "A (sort of) New Image Data Format Standard: NifTI-1" NeuroImage; 2004; vol. 22.
S.M. Smith "Fast robust automated brain extraction" Human Brain Mapping; 2002; vol. 17; No. 3; pp. 143-155.
S.M. Smith et al. "Advances in functional and structural MR image analysis and implementation as FSL" NeuroImage; 2004; vol. 23, No. S1; pp. 208-219.
S.M. Smith et al. "Tract-based spatial statistics: Voxelwise analysis of multi-subject diffusion data" NeuroImage; 2006; vol. 31; pp. 1487-1505.
T. Fawcett "An introduction to ROC analysis" Pattern Recognition Letters; 2006; vol. 27; pp. 861-874.
T. Lescot et al. "Treatment o intrcranialhypertension", Current Opinion Critical Care; 2008; vol. 14; pp. 129-134.
Y.W. Chen et al. "Combining SVMs with various feature selection strategies"; Springer; 2006.

* cited by examiner

< left – right > radiological convention

METHOD FOR QUANTIFYING BRAIN INJURIES

TECHNICAL FIELD

The present invention relates to an ex-vivo method for detecting and/or quantifying brain injuries. The present invention relates also to an ex-vivo method for monitoring the trend of a brain injury, and an ex-vivo method for predicting when a patient will come out of a coma.

The present invention finds an application in particular in the medical field and in the field of clinical studies.

In the description below, the references between square brackets ([ ]) refer to the list of references given at the end of the text.

STATE OF THE ART

In man, cranial traumas are the main cause of death, of coma and of severe handicap before the age of 45. They are due, primarily, to public highway accidents, approximately 50%, sporting accidents, accidents at work, accidents in the home, attacks. For example, it is important to know that cranial trauma corresponds to 75% of the causes of mortality among youths under 30 years of age. It is considered to be a real public health problem.

In France, 180 000 people are currently hospitalized for severe cranial trauma. Generally, a moderate cranial trauma requires hospitalization of approximately 6 months, and a severe cranial trauma 1 year or more. The costs linked to such hospitalizations are colossal. In the United States, excluding civilians, between 180 000 and 320 000 American soldiers have been diagnosed with such trauma since 2000.

Injuries similar to those caused by cranial traumas can also be caused without trauma. They can, for example, be anoxic brain injuries or hemorrhages or hypoglycemic attacks.

These various events represent, in the majority of cases, significant neurological attacks provoking death or incapacity.

After an acute neurological attack, for example primarily after severe cranial trauma, the brain-injured person is often entitled to compensation when there is a responsible third party or it concerns an accident at work. This compensation these days is based on the clinical assessment of the after-effects. However, this clinical assessment remains subjective. With the disorders relating mainly to the higher functions, the analysis of the handicap has specific dimensions, such as the social and professional integration capacity of the injured party, that is often difficult to objectivize. To this can be added neuropsychological disorders such as anosognosia, that is to say the loss of consciousness of one's own problems which render the assessment even more subjective.

The acceptance of liability by the insurance policies, for example sickness insurance and/or complementary insurance policies is currently primarily based on a clinical assessment of the patient. However, this assessment is random, and does not make it possible to determine with any certainty the impact of the trauma.

There is therefore a real need for a procedure and/or a method that makes it possible notably to determine, with 100% reliability, the impact of one or more injuries, in order, for example, to determine the care and the financial compensation due from the insurance.

There are, in the state of the art, methods for quantifying brain injuries based on, for example, routine morphological imaging using a scanner and/or a morphological MRI.

However, the methods known from the prior art do not make it possible to accurately quantify a brain injury, in particular, they do not make it possible to determine and/or detect the injuries to the fibers of the white matter, notably the diffuse injuries, which are the source of the main long-term disorders.

Furthermore, the methods known in the prior art do not make it possible to track the trend of a brain injury, with or without treatment of the patient, in particular an injury to the fibers of the white matter.

There is therefore a real need for a procedure and/or a method that mitigates these defects, shortcomings and obstacles of the prior art, in particular a method that makes it possible notably to detect and quantify the brain injuries.

Furthermore, there is a real need for an effective procedure and/or method that makes it possible notably to track the trend of an injury to the fibers of the white matter and/or that makes it possible to determine, in the case where a patient is in a coma, the probability that the patient will come out of the coma.

DESCRIPTION OF THE INVENTION

The present invention specifically makes it possible to resolve and overcome the obstacles and shortcomings of the prior art mentioned above by providing an ex-vivo method for detecting and/or quantifying brain injuries of a test subject comprising the following steps:

a) measurement of the fractional anisotropy $FA_1$ in at least one first region of the brain on an image obtained by magnetic resonance imaging (MRI) of the brain of a test subject, b) measurement of the axial diffusivity $DA_1$ in at least one second region of the brain on an image obtained by magnetic resonance imaging (MRI) of the brain of a test subject, c) measurement of the radial diffusivity $DR_1$ in at least one third region of the brain on an image obtained by magnetic resonance imaging (MRI) of the brain of a test subject, d) determination of the ratios SFA, SDA, SRD as defined below by comparison of the measured values $FA_1$, $DA_1$, $DR_1$ to normal regional values of fractional anisotropy $FA_n$, of axial diffusivity $DA_n$ and of radial diffusivity $RD_n$ of a reference group of healthy subjects, for said regions according to the following formulae:

$$SFA=(FA_1/FA_n)$$

$$SDA=(DA_1/DA_n)$$

$$SRD=(DR_1/DR_n)$$

said region of the brain being injured if the value of SFA, SDA and/or SRD is greater than or less than 1 plus or minus two times the standard deviation of the regional measurements from the reference group of healthy subjects respectively of the reference fractional anisotropy, axial diffusivity, radial diffusivity in said region of interest.

Another subject of the present invention is an ex-vivo method for monitoring the trend of a brain injury in a test subject comprising the following steps at a time $t_0$ and at a time $t_1$:

a) measurements of the fractional anisotropy $FA_1$ at $t_0$ and $FA_2$ at $t_1$ in at least one first region of the brain on an image obtained by magnetic resonance imaging (MRI) of the brain of a test subject, b) measurements of the axial diffusivity $DA_1$ at $t_0$ and $DA_2$ at $t_1$ in at least one second region of the brain on an image obtained by magnetic resonance imaging (MRI) of the brain of a test subject, c) measurements of the radial diffusivity $DR_1$ at $t_0$ and $DR_2$ at $t_1$ in at least one third region of the brain on an image obtained by magnetic resonance imaging (MRI) of the brain of a test subject, d) determination of the ratios $S_{FA}1$, $S_{DA}1$, $S_{DR}1$, $S_{FA}2$, $S_{DA}2$, and $S_{DR}2$ as defined below by comparison of the measured values $FA_1$, $DA_1$, $DR_1$, $FA_2$, $DA_2$, $DR_2$ against normal regional values of fractional anisotropy $FA_n$, of axial diffusivity $DA_n$ and of radial diffusivity $DR_n$, for said regions according to the following formulae:

$$S_{FA}1=(FA_1/FA_n)$$

$$S_{DA}1=(DA_1/DA_n)$$

$$S_{DR}1=(DR_1/DR_n)$$

$$S_{FA}2=(FA_2/FA_n)$$

$$S_{DA}2=(DA_2/DA_n)$$

$$S_{DR}2=(DR_2/DR_n)$$

e) determination of the variation $\Delta S_{FA}$, $\Delta S_{DA}$, $\Delta S_{DR}$ according to the following formulae:

$$\Delta S_{FA}=S_{FA}2-S_{FA}1$$

$$\Delta S_{DA}=S_{DA}2-S_{DA}1$$

$$\Delta S_{DR}=S_{DR}2-S_{DR}1$$

a negative variation of at least one value $S_{FA}$, $S_{DA}$, indicating an aggravation of the injury, a positive variation of at least one value $S_{FA}$, $S_{DA}$, indicating a recovery, a negative variation of $S_{DR}$ indicating a recovery, a positive variation of $S_{DR}$ indicating an aggravation of the injury.

Another subject of the present invention is an ex-vivo method for predicting outcome from coma, from the vegetative state or from the state of minimal consciousness of a test subject comprising the following steps:

a) measurement of the fractional anisotropy $FA_1$ in at least one first region of the brain on an image obtained by magnetic resonance imaging (MRI) of the brain of a test subject, b) measurement of the axial diffusivity $DA_1$ in at least one second region of the brain on an image obtained by magnetic resonance imaging (MRI) of the brain of a test subject, c) measurement of the radial diffusivity $DR_1$ in at least one third region of the brain on an image obtained by magnetic resonance imaging (MRI) of the brain of a test subject, d) determination of the diffusion ratios $S_{FAp}$, $S_{DAp}$, $S_{DRp}$ by comparison of the measured values $FA_1$, $DA_1$, $DR_1$ against normal regional values of fractional anisotropy $FA_n$, of axial diffusivity $DA_n$ and of radial diffusivity $DR_n$ of a reference group of healthy subjects, for said regions according to the following formulae:

$$S_{FAp}=(FA_1/FA_n)$$

$$S_{DAp}=(DA_1/DA_n)$$

$$S_{DRp}=(DR_1/DR_n)$$

e) determination of a predictive algorithm F from the diffusion ratio $S_{FAref}$; $S_{DAref}$; $S_{DRref}$ of determined regions of the brain of a reference group of subjects as in the abovementioned steps a) to d) and of supervised classification software making it possible to statistically classify the data $S_{FAref}$; $S_{DAref}$; $S_{DRref}$ as a function of the states of outcome from coma, from the vegetative state or from the state of minimal consciousness of the subjects of the reference group;

f) calculation of a prediction value sDTI of the test subject by application of the algorithm F determined in the step e) and of the values $S_{FAp}$; $S_{DAp}$, $S_{DRp}$ obtained in the step d);

g) determination of at least two ranges of prediction values by application of the algorithm F to the diffusion ratios $S_{FAref}$; $S_{DAref}$; $S_{DRref}$ a positive range and a negative range, the positive range delimiting the values for which prediction of outcome from coma, from the vegetative state or from the state of minimal consciousness is favorable, the negative range the reverse, h) comparison of the prediction value of the step f) with said at least two ranges determined in the step g).

Herein, "MRI" should be understood to mean a medical imaging method based on the phenomenon of magnetic resonance, which makes it possible to obtain tomographic images of tissues, for example of soft tissues.

Herein, "MRI image" should be understood to mean any image obtained from an MRI device, for example a 1.5 Tesla, 3.0 Tesla or 7.0 Tesla MRI apparatus, for example from the company Philips, from the company General Electric (GE), or from the company Siemens or from any other company. According to the invention, the MRI image can be any image obtained by an MRI device, for example an unweighted image, preferably a diffusion-weighted image.

Herein, "diffusion-weighted MRI" should be understood to mean a sequence sensitive to the local characteristics of the diffusion of the water molecules in the tissues as described in Basser et al. 1994 [1]. In the brain, the organization of the axons in bundles of fibers induces an anisotropic diffusion of the water molecules, more significant in the direction of the fibers than in the transverse plane. The MRI of the diffusion tensor (DTI) makes it possible to quantify this anisotropy locally by measuring the local diffusion in the three main directions ($\lambda 1$, $\lambda 2$ and $\lambda 3$) of the model of the tensor from diffusion measurements repeated in different directions of the space as described in Basser and Pierpaoli 1996 [2].

The measurements make it possible to measure:
the axial diffusivity or DA equal to $\lambda 1$,
the radial diffusivity or DR equal to $(\lambda 2+\lambda 3)/2$,
the mean diffusivity or MD equal to $(\lambda 1+\lambda 2+\lambda 3)/3$, and
the fractional anisotropy or FA (equal to FA=sqrt($\frac{1}{2}$)×sqrt $(\lambda 1-\lambda 2)^2+(\lambda 1-\lambda 3)^2+(\lambda 2+\lambda 3)^2)$/sqrt($\lambda 1^2+\lambda 2^2+\lambda 3^2$)).

Herein, "region of the brain" should be understood to mean a region selected from the middle cerebellar peduncle (ICBM #1), the anterior brain stem (ICBM #2,7,8), the posterior brain stem (ICBM #9,10,11,12,13,14), the genu of the corpus callosium (ICBM #3), the body of the corpus callosium (ICBM #4), the splenium of the corpus callosium (ICBM #5), the right cerebral peduncle (ICBM #15), the left cerebral peduncle (ICBM #16), the right sagittal stratum (ICBM #21,29,31,47), the left sagittal stratum (ICBM #22, 30,32,48), the right superior longitudinal fasciculus (ICBM #41), the left superior longitudinal fasciculus (ICBM #42), the anterior limb of the right internal capsule (ICBM #17), the anterior limb of the left internal capsule (ICBM #18), the posterior limb of the right internal capsule (ICBM #19), the posterior limb of the left internal capsule (ICBM #20), the right external capsule (ICBM #33), the left external capsule (ICBM #34), the right corona radiata (ICBM #23,25,27), the left corona radiata (ICBM #24,26,28).

According to the invention, the measurements of fractional anisotropy, axial diffusivity, radial diffusivity can be performed independently in at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty of the regions of the brain cited above. Measurements in other regions of the brain can also be performed.

According to the invention, the measurements of fractional anisotropy, axial diffusivity, radial diffusivity can be performed in all the abovementioned regions, namely the middle cerebellar peduncle (ICBM #1), the anterior brain stem (ICBM #2,7,8), the posterior brain stem (ICBM #9,10,11,12,13,14), the genu of the corpus callosium (ICBM #3), the body of the corpus callosium (ICBM #4), the splenium of the corpus callosium (ICBM #5), the right cerebral peduncle (ICBM #15), the left cerebral peduncle (ICBM #16), the right sagittal stratum (ICBM #21,29,31,47), the left sagittal stratum (ICBM #22,30,32,48), the right superior longitudinal fasciculus (ICBM #41), the left superior longitudinal fasciculus (ICBM #42), the anterior limb of the right internal capsule (ICBM #17), the anterior limb of the left internal capsule (ICBM #18), the posterior limb of the right internal capsule (ICBM #19), the posterior limb of the left internal capsule (ICBM #20), the right external capsule (ICBM #33), the left external capsule (ICBM #34), the right corona radiata (ICBM #23,25,27), the left corona radiata (ICBM #24,26,28).

Herein, "ICBM #n" refers to the nth region of the atlas of 48 regions of white matter constructed from diffusion data from 81 healthy subjects (the 'ICBM-DTI-81' atlas (Mori et al. 2005 [9]) available in the FSL software (Smith et al. 2004 [7]).

Herein, said at least one first region of the brain, said at least one second region of the brain, said at least one third region of the brain can be independently identical or different.

Herein, "brain injury" means any injury likely to have affected the brain, for example a brain injury and/or a cranial trauma, notably that can be caused by a physical impact, and/or a hemorrhage, for example a meningeal hemorrhage, for example an aneurismal meningeal hemorrhage, an intracerebral hematoma, spontaneous or secondary to a vascular pathology and/or an ischemic attack and/or a hemorrhagic attack, for example an intraparenchymal hemorrhagic attack and/or cerebral anoxia, for example following a cardiac or circulatory arrest.

According to the invention "test subject" means a patient having suffered an injury as mentioned above. It can be, for example, any living being with a brain, for example a human or an animal, regardless of age and sex.

Herein, "reference group of subjects" means a group comprising at least 10 reference subjects as defined above, for example at least 40, at least 60, at least 100 reference subjects. It can for example be a group comprising 30 to 500 subjects, 40 to 200 subjects, 45 to 110 reference subjects.

Herein, "reference healthy subject" means a being with a brain, for example a human being or an animal, not having suffered any impact, hemorrhage, circulatory problem or cardiac arrest, or any other bodily impairment likely to lead to an injury as defined above. It can be a subject that is the same as or different from the test subject.

The method of the invention is advantageously performed from $FA_n$, $DA_n$ and $RD_n$ values measured on a "reference group of healthy subjects". "Reference group of healthy subjects" means a group of living beings with a brain, for example a group of human beings or of animals, preferably identical in their species, regardless of age and sex, preferably of the same age and/or from the same age range, with respect to the test subject, and of the same sex as that of the test subject.

Herein, "age range" means preferably +/−10 years relative to the test subject, preferably +/−9 years, preferably +/−8 years, preferably +/−7 years, preferably +/−6 years, preferably +/−5 years, preferably +/−5 years, preferably +/−5 years, preferably +/−5 years, preferably +/−4 years, preferably +/−3 years, preferably +/−2 years, preferably +/−1 year.

Herein, "normal values" means, independently, the values of fractional anisotropy, of radial diffusion and/or of axial diffusion measured in a given region in a reference healthy subject, or in a reference group of healthy subjects, as defined above. They can, for example, be reference average values measured for a given region of the brain as defined above in at least one reference healthy subject or one reference group of healthy subjects.

According to the invention, these normal values can also have been measured in the test subject before he or she suffered the shock, hemorrhage, circulatory problem or cardiac arrest, or any other bodily impairment likely to lead to an injury as defined above. They can, for example, be measurements performed on a patient at risk from one of the abovementioned causes of brain injury, for example a person exhibiting a cardiac insufficiency, heart rate disorders, a hypercholesterolemia, an asymptomatic intracranial aneurism, an intracerebral vascular epathology, for example an asymptomatic arteriovenous malformation, an amyloid angiopathy and/or any other intracerebral vascular pathology and/or a neurological after-effect.

According to the invention, the method for detecting and/or quantifying brain injuries of the present invention can further comprise a step f) of determination of the intensity of the injuries by measurement of the variation against the average of the reference values. This can, for example, be calculation of the intensity of the injuries by region ($I_{les}$) according to the following formula:

$$I_{les}=(((FA_1-FA_{ref})\times 100)/FA_{ref})+(((DA_1-DA_{ref})\times 100)/DA_{ref})+(((DR_1-DR_{ref})\times 100)/DR_{ref}).$$

According to the invention, in the ex-vivo method for monitoring the trend of a brain injury in a test subject, the measurements at the time $t_0$ can be performed on an MRI image taken in a period of 1 to 180 days, for example following a brain injury, of 1 hour to 31 days, of 1 hour to 48 hours, or within a time limit of less than 31 days.

Herein, the measurements at the time $t_1$ can be performed on an MRI image taken within a period of approximately 1 to several months, for example from 1 to 12 months, for example from 1 to 9 months, for example 6 months, from 1 to 6 months, for example 3 months, from 1 to 3 months, from approximately 1 year to several years, for example from 1 to 30 years, from 1 to 20 years, from 1 to 10 years, from 1 to 5 years, from 1 to 3 years, from 1 to 2 years according to the measurements at the time $t_0$.

The present invention is advantageously applicable in the medical field where it will be able to be used, for example, in clinical trials in order to detect and quantify injuries to the brain, during a period of remission, for example following a brain trauma of any kind or of traumatic, anoxic or hemorrhagic origin.

Furthermore, the method of the invention advantageously makes it possible to obtain a reliable and reproducible result which can be compared between patients, at different times. It can thus make it possible, advantageously, for example, to compare the recovery capabilities according to the trauma, the patient, the medicinal treatment or physical treatments or any other re-education treatment undertaken.

The method of the present invention also advantageously makes it possible to correlate the trend of an injury with the trend of the after-effects and/or the appearance of after-effects in a test subject. The present invention can also make it possible to perform mappings between the injuries and/or after-effects as quantified by MRI with those assessed clinically.

According to the invention, "prediction value" means the value or score obtained after the application of the algorithm F in the step g) of the ex-vivo method for predicting outcome from coma, from the vegetative state or from the state of minimal consciousness of a test subject.

According to the invention, in the ex-vivo method for predicting outcome from coma, from the vegetative state or from the state of minimal consciousness of a test subject, the step g) of determination of at least two ranges can be performed via the comparison of the results obtained following the application of the predictive algorithm F and the fate of the corresponding reference subjects. In other words, the scores/results obtained after application of the predictive algorithm F can be correlated with the fate of the patient, in particular his or her outcome from coma, from the vegetative state or from the state of consciousness. This correlation makes it possible, for example, to determine ranges of prediction values within which the probability of outcome or not from coma, from the vegetative state or from the state of minimal consciousness is 100% certain and reliable.

Another subject of the present invention is the use of supervised classification software to construct an ex-vivo diagnostic reference base for predicting outcome from coma, from the vegetative state or from the state of minimal consciousness of a test subject.

Another subject of the present invention is the use of a reference base obtained by means of supervised classification software in an ex-vivo diagnostic method for predicting outcome from coma, from the vegetative state or from the state of minimal consciousness of a test subject.

"Supervised classification software" means software capable of implementing, from a reference (or learning) database, a prediction algorithm (or function) denoted F which, with an input x, associates an output F(x). The supervised learning algorithm generalizes, for new inputs, a decision rule determined from known and appraised data.

Such supervised classification software constitutes means for implementing supervised classification methods.

Supervised classification methods that can be cited include, for example, neural networks, the k closest neighbors method, decision trees or support vector machines. These methods are implemented for example in the software R (http://www.r-project.org/) or the software LIBSVM (http://www.csie.ntu.edu.twi/~cjlin/libsvm/).

"Reference base" means a database constructed from reference subjects. These data are obtained from diffusion tensor MRI measurements of determined regions of the brain of said patients as in the abovementioned steps a) to d). According to the invention, these measurements are introduced into supervised classification software which determines an algorithm, linear or not, that makes it possible, by the separation of the values, to both compute a prediction value and define ranges of prediction values.

In other words, the ratios obtained in the step d) of the method from several test subjects can constitute a reference base likely to be used in supervised classification software which determines an algorithm, linear or not, that makes it possible, by the separation of the values and to both compute a prediction value and define ranges of prediction values.

These ranges of prediction values define ranges of positive, indecisive or negative values as defined above.

This reference base is designed to be open-ended in particular to be enriched with the number of reference subjects constituting said base.

According to the invention, advantageously when implementing the method for predicting outcome from coma, from the vegetative state or from the state of minimal consciousness according to the invention, the reference subjects may or may not have brain injuries and can make it possible to construct said reference base. There can be, for example, a reference set of subjects or group of subjects as defined above, having brain injuries, and possibly of healthy subjects in order to form a complete reference base making it possible to represent all the possible states of a tested subject.

According to the invention, the subjects of the base can be subjects in coma, in a vegetative state or a state of minimal consciousness or not. There can also be subjects having brain injuries. What is understood by "brain injury" is defined above. The injuries can be caused for example by a cranial trauma, a cerebral anoxia or an intracranial aneurismal rupture.

According to the invention "coma" means a complete abolition of the life functions of relationship, without opening the eyes, while the functions of vegetative life are retained.

According to the invention, "vegetative state" means a corruption of brain operations so deep that the patients wake up from the coma, that is to say that they open the eyes, without regaining consciousness. They have lost their cognitive functions and all possibility of relational life. Only a few vital functions remain: waking-sleeping cycles, breathing, sometimes swallowing. This state is called "chronic" when it persists for longer than one year in the case of traumatic injuries, or more than three months in the case of anoxic injuries.

According to the invention, "state of minimal consciousness", means a subject incapable of consistently following simple instructions, for example grip the hand, but who nevertheless demonstrates a state of consciousness of his or her environment by responding to certain stimuli, for example by tears, by smiles, or other emotional expressions. The response to commands is fluctuating and irregular.

According to the invention, advantageously when implementing the method for predicting outcome from coma, from the vegetative state or from the state of minimal consciousness according to the invention, the measurement of the fractional anisotropy of the step a) can be performed in at least one, 2, or 3, or 4 or 5 or 6 or 7 or 8 or 9 or 10 of the regions of the brain selected from the group comprising the middle cerebellar peduncle (ICBM #1), the anterior brain stem (ICBM #2,7,8), the posterior brain stem (ICBM #9,10, 11,12,13,14), the genu of the corpus callosium (ICBM #3), the body of the corpus callosium (ICBM #4), the splenium of the corpus callosium (ICBM #5), the right cerebral peduncle (ICBM #15), the left cerebral peduncle (ICBM #16), the sagittal stratum, the anterior limb of the right internal capsule (ICBM #17), the anterior limb of the left internal capsule (ICBM #18).

According to the invention, advantageously when implementing the method for predicting outcome from coma, from the vegetative state or from the state of minimal consciousness according to the invention, the measurement of the radial diffusivity of the step c) can be performed in at least one; 2, or 3, or 4 or 5 or 6 or 7 or 8 or 9 or 10 or 11 of the regions of the brain selected from the group comprising the cerebellar peduncle, the anterior brain stem (ICBM #2,7,8), the posterior brain stem (ICBM #10), the genu of the corpus callosium (ICBM #3), the body of the corpus callosium (ICBM #4), the right cerebral peduncle (ICBM #15), the left cerebral peduncle (ICBM #16), the anterior limb of the left internal capsule (ICBM #18), the posterior limb of the right internal capsule (ICBM #19), the posterior limb of the left internal capsule (ICBM #20).

According to the invention, advantageously when implementing the method for predicting outcome from coma, from the vegetative state or from the state of minimal consciousness according to the invention, the measurement of the axial diffusivity of the step b) can be performed in at least one, 2, or 3, or 4 or 5 of the regions of the brain selected from the group comprising the posterior brain stem (ICBM #10), the genu of the corpus callosium (ICBM #3), the splenium of the corpus callosium (ICBM #5), the left cerebral peduncle (ICBM #16), the posterior limb of the left internal capsule (ICBM #20).

According to the invention, the method for predicting outcome from coma, from the vegetative state or from the state of minimal conciousness, the method can further comprise a step i) of determining outcome from coma, from the vegetative state or from the state of minimal consciousness by comparison of the prediction value obtained with the prediction ranges, the outcome from coma being predicted if the value obtained lies within the positive range, non-outcome from coma being predicted if the value lies within the negative range.

Another subject of the present invention is an ex-vivo method for predicting outcome from coma, from the vegetative state or from the state of minimal consciousness of a test subject comprising the following steps:
a) measurement of the fractional anisotropy FA in at least one first region of the brain on an image obtained by magnetic resonance imaging (MRI) of the brain of a test subject,
b) measurement of a score according to the following formula:

$$scoreDTI = \frac{1}{1 + e^{beta_0} + \sum_i beta_i \cdot X_i}$$

in which $X_i$ represents the measurement values of the fractional anisotropy FA, $beta_o$ is a real number and $beta_i$ are real numbers,
c) a DTI score lying between 0 and 0.83 indicating a favorable prediction of outcome from coma, from the vegetative state or from the state of minimal conciousness, a DTI score of between 0.83 and 1 indicating an unfavorable prediction of outcome from coma, from the vegetative state or from the state of minimal conciousness.

The test subject, the region of the brain, the fractional anisotropy measurement are as defined above.

According to the invention, the $beta_o$ and $beta_i$ values can be real numbers as described in the table below:

| Regions | $beta_i$ |
|---|---|
| Middle cerebellar peduncle (ICBM #1) | from 0.0 to 0.0 |
| Anterior brain stem (ICBM #2, 7, 8) | from 0.0 to 0.0 |
| Posterior brain stem (ICBM #9, 10, 11, 12, 13, 14) | from 0.0 to 0.0 |
| Genu of the corpus callosium (ICBM #3) | from 6.466252753 to 7.28446365 |
| Body of the corpus callosium (ICBM #4) | from 3.636447939 to 4.502330614 |
| Splenium of the corpus callosium (ICBM #5) | from 11.42226758 to 12.288150254 |
| Right cerebral peduncle (ICBM #15) | from −5.208057762 to −4.493633664 |
| Left cerebral peduncle (ICBM #16) | from 1.277114354 to 2.596620002 |
| Right sagittal stratum (ICBM #21, 29, 31, 47) | from 3.795844311 to 4.669302645 |
| Left sagittal stratum (ICBM #22, 30, 32, 48) | from −3.80915557531 to −2.87934927167 |
| Right superior longitudinal fasciculus (ICBM #41) | from −7.26452800004 to −6.43552940029 |
| Left superior longitudinal fasciculus (ICBM #42) | from −5.33860234505 to −4.65103436119 |
| Anterior limb of the right internal capsule (ICBM #17) | from 0.73250989 to 2.43884734109 |
| Anterior limb of the left internal capsule (ICBM #18) | from 6.86347919816 to 7.58775407373 |
| Posterior limb of the right internal capsule (ICBM #19) | from 1.52413579894 to 2.22785801866 |
| Posterior limb of the left internal capsule (ICBM #20) | from −0.638297963914 to 0.17271458225 |
| Right external capsule (ICBM #33) | from 6.0227582126 to 10.560807638 |
| Left external capsule (ICBM #34) | from −0.378850609298 to 0.423449686126 |
| Right corona radiata (ICBM #23, 25, 27) | from −0.410910494678 to 0.292109783525 |
| Left corona radiata (ICBM #24, 26, 28) | from −0.331246786435 to 7.783966523 |
| $beta_0$ | from −21.034986402 to −24.317724924 |

According to the invention, advantageously when implementing the method for predicting outcome from coma, from the vegetative state or from the state of minimal consciousness according to the invention, the measurement of the fractional anisotropy of the step a) can be performed in at least 4 or 5 or 6 or 7 or 8 or 9 or 10 or all of the regions of the brain selected from the group comprising the middle cerebellar peduncle (ICBM #1), the anterior brain stem (ICBM #2,7,8), the posterior brain stem (ICBM #9,10,11, 12,13,14), the genu of the corpus callosium (ICBM #3), the body of the corpus callosium (ICBM #4), the splenium of the corpus callosium (ICBM #5), the right cerebral peduncle (ICBM #15), the left cerebral peduncle (ICBM #16), the right sagittal stratum (ICBM #21,29,31,47), the left sagittal stratum (ICBM #22,30,32,48), the right superior longitudinal fasciculus (ICBM #41), the left superior longitudinal fasciculus (ICBM #42), the anterior limb of the right internal capsule (ICBM #17), the anterior limb of the left internal capsule (ICBM #18), the posterior limb of the right internal capsule (ICBM #19), the posterior limb of the left internal capsule (ICBM #20), the right external capsule (ICBM #33), the left external capsule (ICBM #34), the right corona radiata (ICBM #23,25,27), the left corona radiata (ICBM #24,26,28).

Advantageously, when implementing the method for predicting outcome from coma, from the vegetative state or from the state of minimal consciousness according to the invention, when the measurement of the fractional anisotropy of the step a) is performed in at least 4 regions of the brain, they can be from the following regions: the left cerebral peduncle (ICBM #16), the anterior limb of the right internal capsule (ICBM #17), the anterior limb of the left internal capsule (ICBM #18), the right external capsule (ICBM #33), the left corona radiata (ICBM #24,26,28).

Advantageously, when implementing the method for predicting outcome from coma, from the vegetative state or from the state of minimal consciousness according to the invention, when the measurement of the fractional anisotropy of the step a) is performed in the 20 regions of the brain mentioned above, the $beta_i$ values can lie within and/or be equal to the values mentioned in the table below:

| Regions | $beta_i$ | Preferred $beta_i$ |
|---|---|---|
| Middle cerebellar peduncle (ICBM #1) | from 0.0 to 0.0 | 0.0 |
| Anterior brain stem (ICBM #2, 7, 8) | from 0.0 to 0.0 | 0.0 |
| Posterior brain stem (ICBM #9, 10, 11, 12, 13, 14) | from 0.0 to 0.0 | 0.0 |
| Genu of the corpus callosium (ICBM #3) | from 6.466252753 to 7.28446365 | 6.87535790908 |
| Body of the corpus callosium (ICBM #4) | from 3.636447939 to 4.502330614 | 4.06938927662 |
| Splenium of the corpus callosium (ICBM #5) | from 11.42226758 to 12.288150254 | 11.855208917 |
| Right cerebral peduncle (ICBM #15) | from −5.208057762 to −4.493633664 | −4.85084571328 |
| Left cerebral peduncle (ICBM #16) | from 1.723161668 to 2.596620002 | 2.15989083485 |
| Right sagittal stratum (ICBM #21, 29, 31, 47) | from 3.795844311 to 4.669302645 | 4.2325734777 |
| Left sagittal stratum (ICBM #22, 30, 32, 48) | from −3.80915557531 to −2.87934927167 | −3.34425242349 |
| Right superior longitudinal fasciculus (ICBM #41) | from −7.26452800004 to −6.43552940029 | −6.85002870016 |
| Left superior longitudinal fasciculus (ICBM #42) | from −5.33860234505 to −4.65103436119 | −4.99481835312 |
| Anterior limb of the right internal capsule (ICBM #17) | from 1.6587492639 to 2.43884734109 | 2.0487983025 |
| Anterior limb of the left internal capsule (ICBM #18) | from 6.86347919816 to 7.58775407373 | 7.22561663595 |
| Posterior limb of the right internal capsule (ICBM #19) | from 1.52413579894 to 2.22785801866 | 1.8759969088 |
| Posterior limb of the left internal capsule (ICBM #20) | from −0.638297963914 to 0.17271458225 | −0.232791690832 |
| Right external capsule (ICBM #33) | from 6.0227582126 to 6.76329905685 | 6.39302863473 |
| Left external capsule (ICBM #34) | from −0.378850609298 to 0.423449686126 | 0.0222995384139 |
| Right corona radiata (ICBM #23, 25, 27) | from −0.410910494678 to 0.292109783525 | −0.0594003555767 |
| Left corona radiata (ICBM #24, 26, 28) | from −0.331246786435 to 0.62156911529 | 0.145161164427 |
| $beta_0$ | from −24.725252173 to −24.317724924 | −24.5214885485 |

The inventors have demonstrated, surprisingly, that the method of the present invention comprising the calculation of the DTI score with the measurement of the FA in at least four regions of the brain advantageously makes it possible to obtain a score allowing for an unfavorable prediction with a sensitivity and a specificity of 73% and 100% respectively.

Advantageously, when implementing the method for predicting outcome from coma, from the vegetative state or from the state of minimal consciousness according to the invention, when the measurement of the fractional anisotropy of the step a) is performed in the following 4 regions of the brain: the left cerebral peduncle (ICBM #16), the anterior limb of the right internal capsule (ICBM #17), the anterior limb of the left internal capsule (ICBM #18), the right external capsule (ICBM #33), the left corona radiata (ICBM #24,26,28), the values of $beta_i$ can be between and/or equal to the values mentioned in the table below:

| Regions | $beta_i$ | Preferred $beta_i$ |
|---|---|---|
| Left cerebral peduncle (ICBM #16) | from 1.277114354 to 2.466668701 | 1.87189152758 |
| Anterior limb of the right internal capsule (ICBM #17) | from 0.73250989 to 1.657549987 | 1.19502993841 |
| Anterior limb of the left internal capsule (ICBM #18) | from 1.296825232 to 2.16904842 | 1.7329368258 |
| Right external capsule (ICBM #33) | from 9.754756364 to 10.560807638 | 10.1577820013 |
| Left corona radiata (ICBM #24, 26, 28) | from 6.9999277456 to 7.783966523 | 7.3919471341 |
| $beta_0$ | from −21.034986402 to −20.522064457 | −20.7785254295 |

Advantageously, the implementation of the method according to the present invention comprising the calculation of the DTI score with the measurement of the FA in four selected regions of the brain makes it possible to increase the sensitivity and the specificity of the DTI score.

Advantageously, the method of the present invention comprising the calculation of the DTI score makes it possible to predict, in a reliable and reproducible manner, outcome from coma, from the vegetative state or from the state of minimal consciousness of a subject. In particular, the method of the present invention makes it possible to obtain a score allowing for a prediction with a sensitivity and a specificity of 80% and 100% respectively.

Another subject of the present invention is a computer program comprising program code instructions for executing the steps of the method according to the invention, when said program is executed on a computer.

The present invention makes it possible, for the first time, to obtain results of measurements of brain injuries that are objective and reliable, reproducible and comparable between patients.

The method of the present invention is also the first that makes it possible to determine, in a reliable, reproducible and quantifiable manner, the percentage of brain injuries and the impacts and clinical trends and ultimate realistic after-effects for the patient.

The present invention is advantageously applicable in the medical field where it can be used, for example, in order to detect and quantify injuries to the brain, notably in order for the practitioner to be able to take appropriate clinical and/or pharmacological decisions for the treatment of the patient.

The present invention can thus be advantageously used in determining the scale and ultimate effects of post-traumatic after-effects and/or in determining financial damages following a traumatic accident and/or any brain trauma occurring for example in an accident, for example a car accident, a two-wheeler accident, pedestrians run over by a motor vehicle on the public highway, accident at work from falling in particular, and/or a trauma in pursuing a sport, for example rugby, boxing, wrestling, notably in cases of issues as to liability and/or acceptance of costs and damages by an insurer or any other personal or professional damage proceeding.

The method of the present invention is advantageously applicable in the medical field where it will be able to be used in order to reliably predict the prediction percentage of outcome from coma, from the vegetative state or from the state of minimal consciousness of a test subject. Furthermore, for example, the method of the invention will advantageously make it possible to determine whether a treatment, for example during clinical trials, can influence the probability of outcome from coma, from the vegetative state or from the state of minimal consciousness of a patient, thus showing the possible benefits of the treatment. The method for predicting outcome from coma, from the vegetative state or from the state of minimal consciousness of the present invention also makes it possible to avoid a possible use of intensive treatment, for example for test patients in a coma, in a vegetative state or a state of minimal consciousness who will certainly never come out of said state.

Furthermore, the method of the invention advantageously makes it possible to obtain a result that is reliable and reproducible and which can be compared between patients, at different times, notably, for example, as a function of the taking of a medicinal treatment or any physical or neurological re-education intervention.

Other advantages will also become apparent to those skilled in the art on reading the following examples, illustrated by the attached figures, given by way of illustration.

BRIEF DESCRIPTION OF THE FIGURES

FIG. 2 B is a bar chart representing the average values of the standardized regional FAs measured on the regions of the corpus callosium, namely the genu of the corpus callosium (ICBM #3), the body of the corpus callosium (ICBM #4) and the splenium of the corpus callosium (ICBM #5). The dark bars represent the values obtained in patients without after-effects one year after the accident, the light bars the values obtained in the patients with neuropsychological after-effects one year after the accident.

FIG. 2 C is a diagram representing the average values of the standardized regional FAs measured on the higher regions of the brain, namely the right sagittal stratum (ICBM #21,29,31,47), the left sagittal stratum (ICBM #22,30,32, 48), the right superior longitudinal fasciculus (ICBM #41), the left superior longitudinal fasciculus (ICBM #42), the anterior limb of the right internal capsule (ICBM #17), the anterior limb of the left internal capsule (ICBM #18), the posterior limb of the right internal capsule (ICBM #19), the posterior limb of the left internal capsule (ICBM #20), the right external capsule (ICBM #33), the left external capsule (ICBM #34), the right corona radiata (ICBM #23,25,27), and the left corona radiata (ICBM #24,26,28). The dark curves represent the values obtained in patients without after-effects one year after the accident (SS), the light curves the values obtained in patients with neuropsychological after-effects one year after the accident (AS).

In FIGS. 2 A to 2 C, the meanings of the abbreviations are as follows: MCP: middle cerebellar peduncle; aBS: anterior brain stem; pBS: posterior brain stem; CP_R: right cerebral peduncle; CP_L: left cerebral peduncle; gCC: genu of the corpus callosium; bCC: body of the corpus callosium; sCC: splenium of the corpus callosium; EC: external capsule; SS: sagittal stratum; SLF: superior longitudinal fasciculus; CR: corona radiata; PLIC: posterior limb of the internal capsule; ALIC: anterior limb of the internal capsule.

Figure 4A:
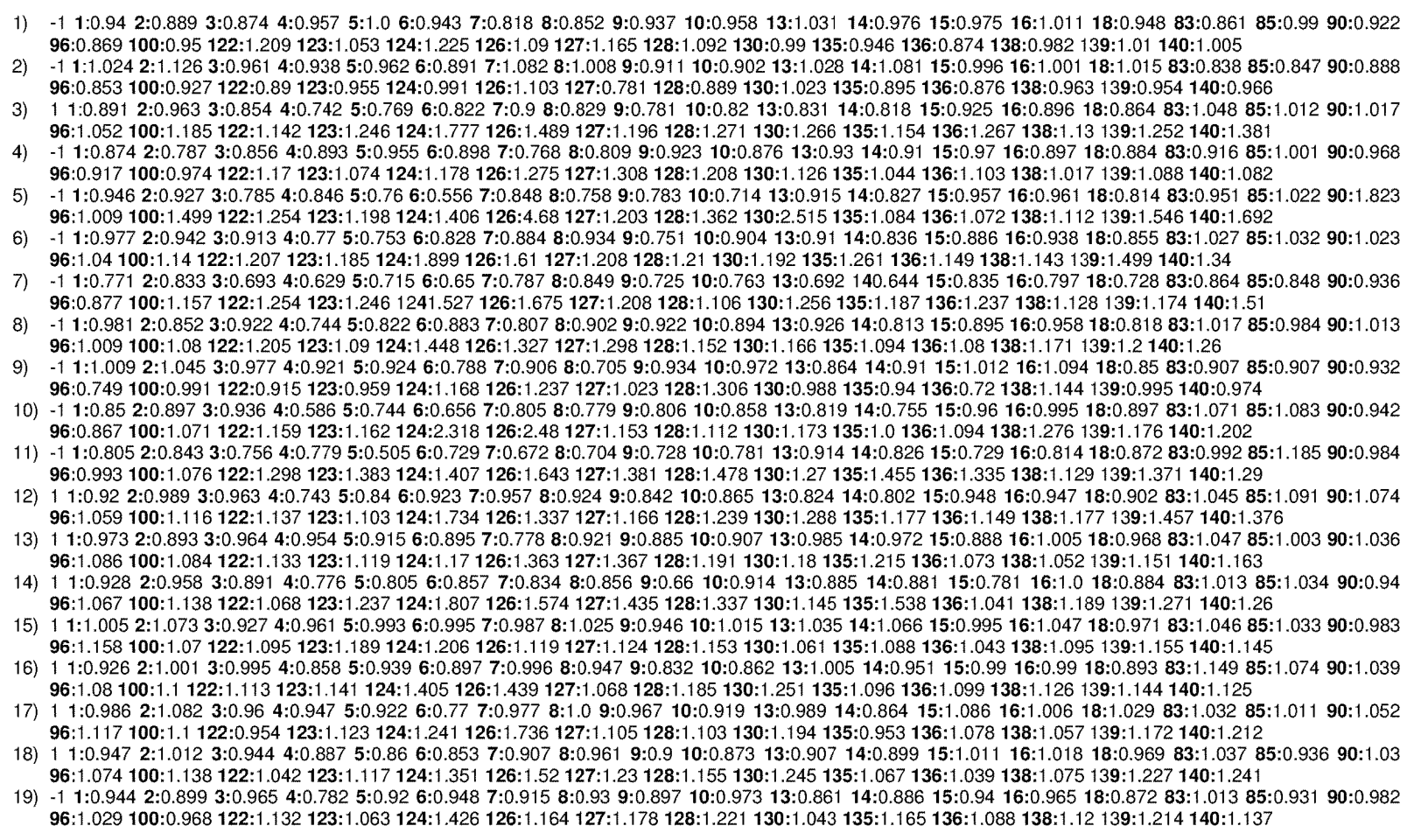
Figure 4B:
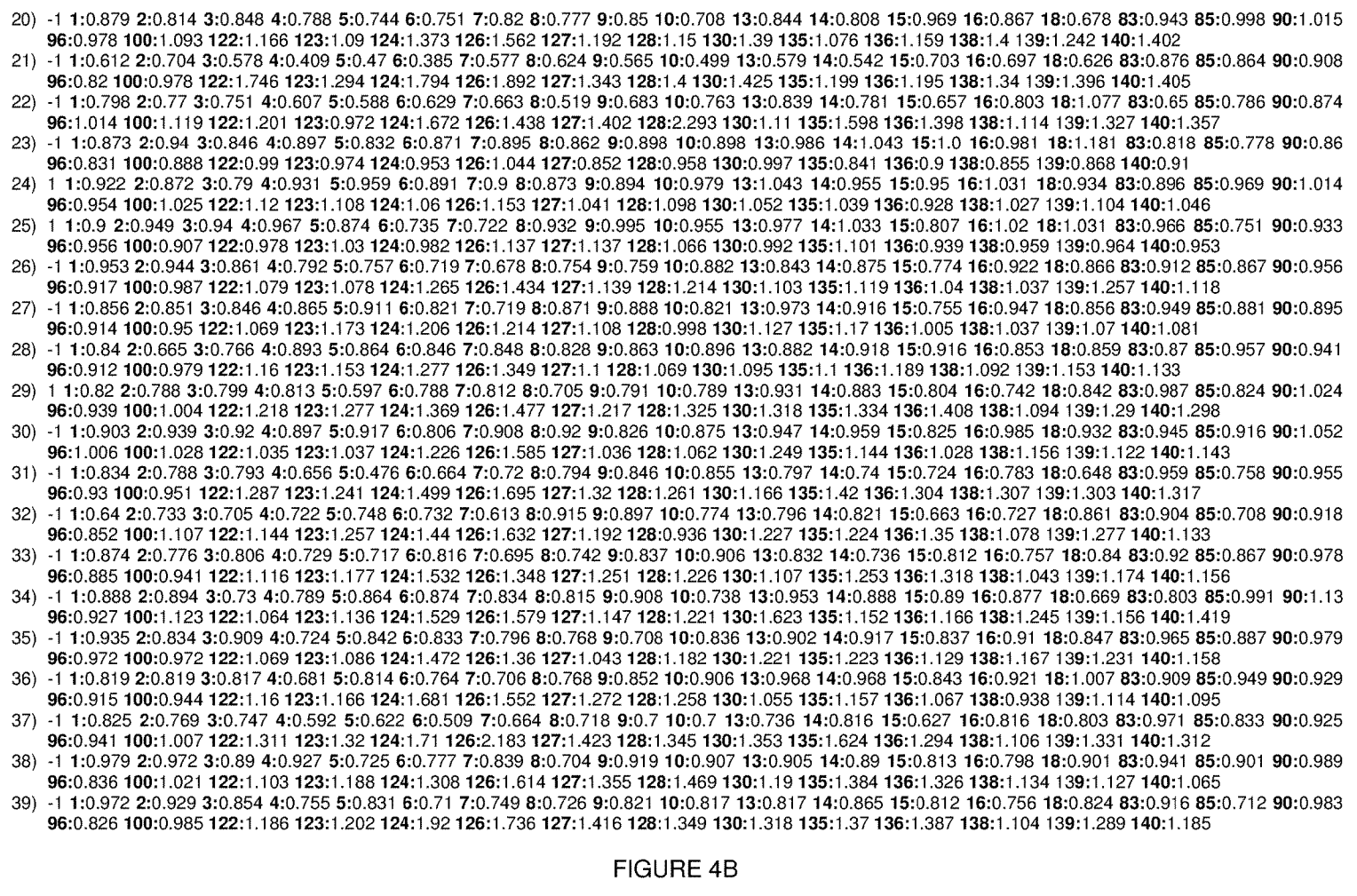
Figure 4D:
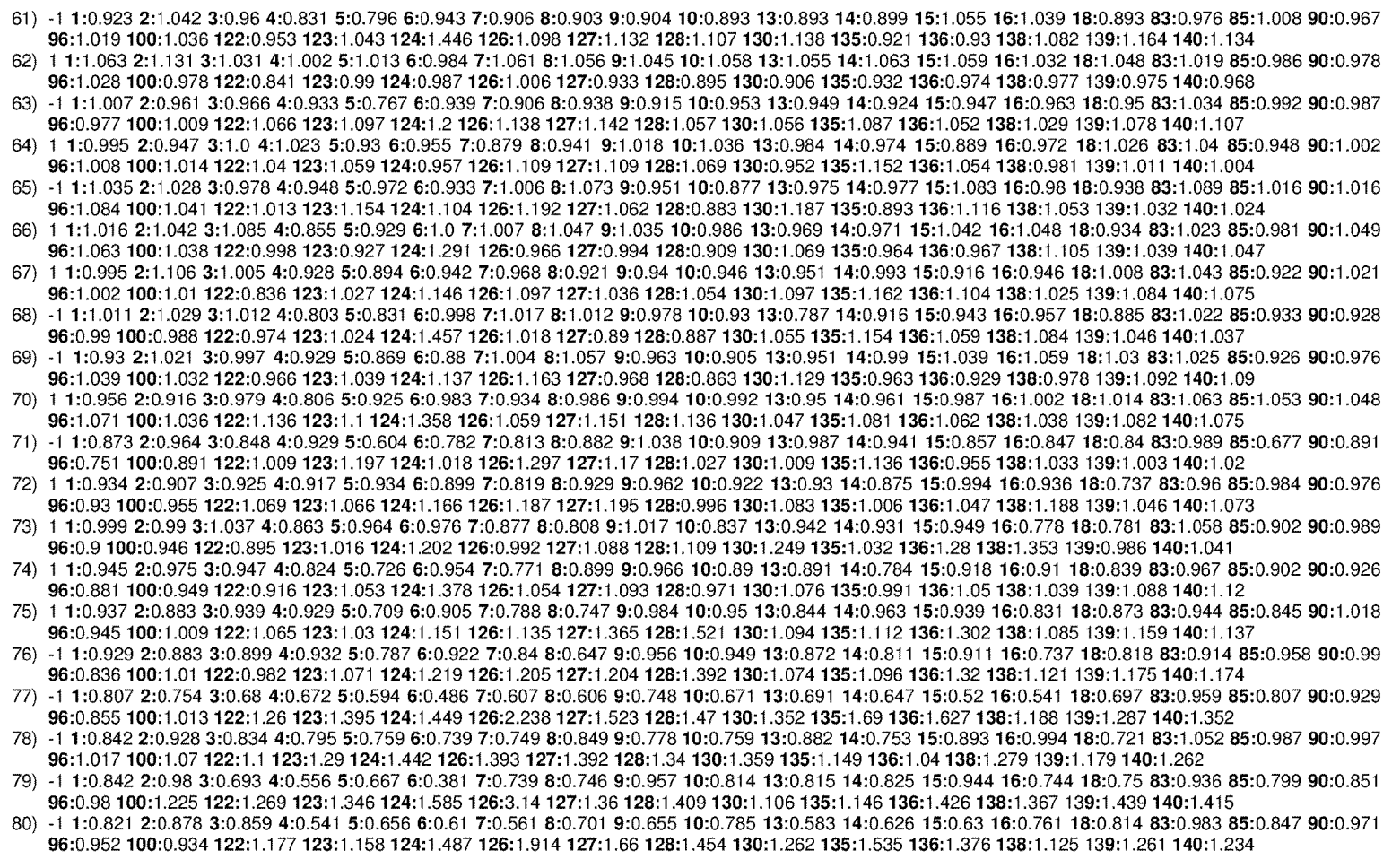
Figure 4F:
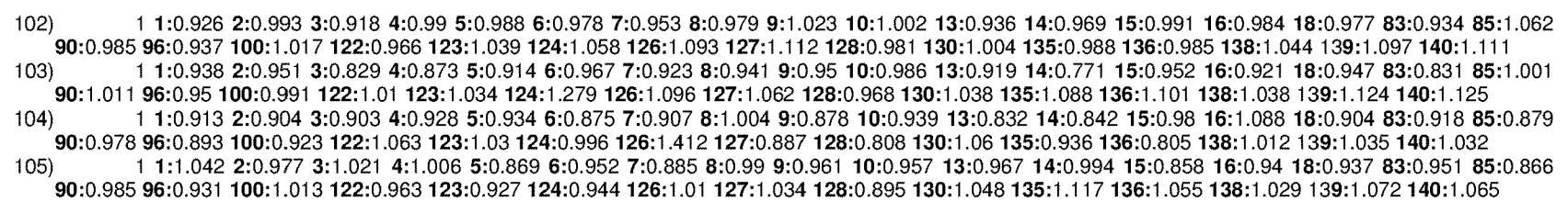

FIG. 4 represents the values obtained for the 32 variables used by the algorithm F of the supervised classification software for the 105 patients of the reference base. In this figure, the numbers in bold indicate the number of the variables as defined in Table 6.

EXAMPLES

Example 1: Implementation of the Method for Quantifying Brain Injuries

The method for quantifying brain injuries, in particular for regional quantification of the injuries of the white matter fibers of the brain relies on the measurements of fractional anisotropy (FA) reflecting the overall integrity of the fibers, of axial diffusivity (AD) reflecting the axonal integrity and of radial diffusivity (DR) reflecting the integrity of the myelin sheath.

For this, it is made up of a number of successive steps:
1. An MRI acquisition of the diffusion tensor (DTI) comprising a T2-weighted acquisition (corresponding to a factor b=0) and acquisitions with diffusion-weighted gradients (b~=1000 s/mm$^2$). To apply the model of the tensor, the acquisition with gradients in at least 6 different directions of the space is necessary.
2. A series of preprocessing of the raw DTI data was performed using the FSL software (http://www.fmrib.ox-.ac.uk/fsl/, Smith et al. 2004 [7]).
3. Correction of the distortions induced by the eddy currents (with the "eddy correct" function). This correction consisted in re-registering (rigid re-registration) the diffusion-weighted volumes on the T2-weighted volume as described in Jenkinson et al. 2002 [4].
4. Extraction of the mask of the brain by removing from the volume all the non-brain tissues (with the bet function) as described in Smith 2002 [6].
5. Calculation of the 3 specific values ($\lambda 1$, $\lambda 2$ and $\lambda 3$) of the model of the tensor for each voxel as described in Basser et al. 1996 [2] making it possible to calculate parametric maps of FA, AD and DR (with the dtifit function).

In order to compare the parametric maps to the reference maps (calculated on controlled healthy subjects and on appraised groups of patients), the latter were projected into a standard space.

For that, the individual FA maps were first of all re-registered by a nonlinear FNIRT re-registration ("FMRIB's Non-linear Image Registration Tool") Andersson et al. 2007a [10], Andersson et al. 2007b [11] in a reference space characterized by a reference image calculated on 58 healthy subjects (FMRIB58_FA). To take into account only maximum values of FA along the bundles, these maximum local values were projected onto the skeleton of the main FA bundles according to the TBSS method described in Smith et al. 2006 [8]. This skeleton represents the centers common to the group of the main bundles of white matter in the brain. The corresponding values of AD and DR were projected onto the same skeleton according to the same transformation.

Figure 2A:
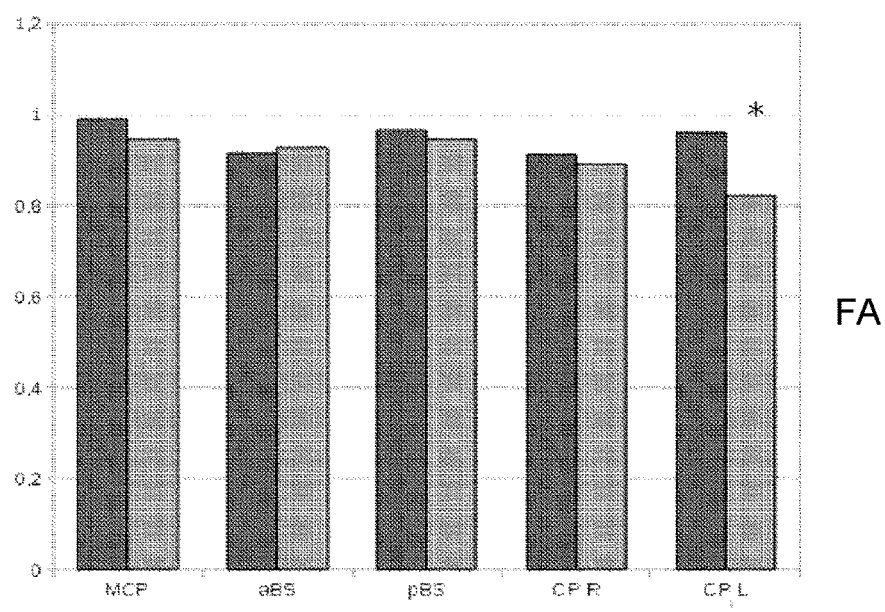
FIG. 2 A is a bar chart representing the average values of the standardized regional FAs measured in the deep regions of the brain, namely the middle cerebellar peduncle (ICBM #1), the anterior brain stem (ICBM #2,7,8), the posterior brain stem (ICBM #9,10,11,12,13,14), the right cerebral peduncle (ICBM #15) and the left cerebral peduncle (ICBM #16). The dark bars represent the values obtained in patients without after-effects one year after the accident, the light bars the values obtained in patients with neuropsychological after-effects one year after the accident.
Figure 2B:
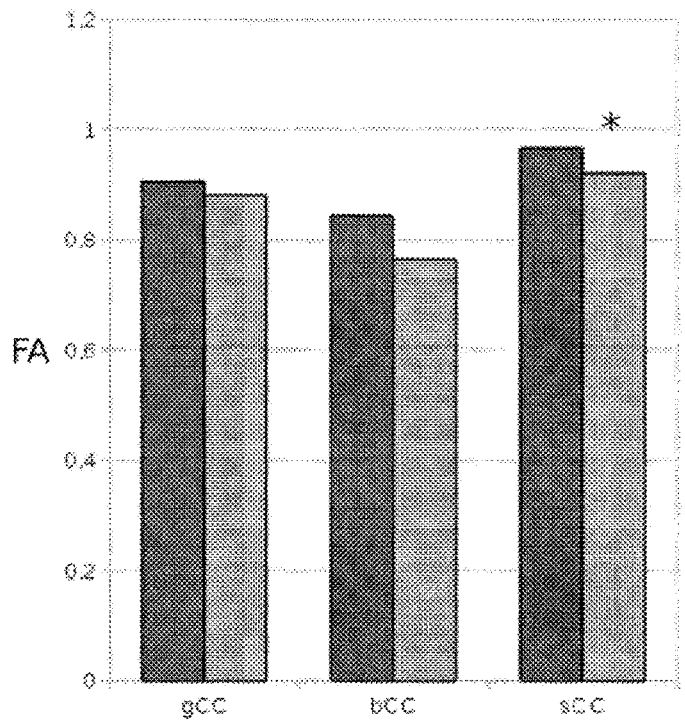
Figure 2C:
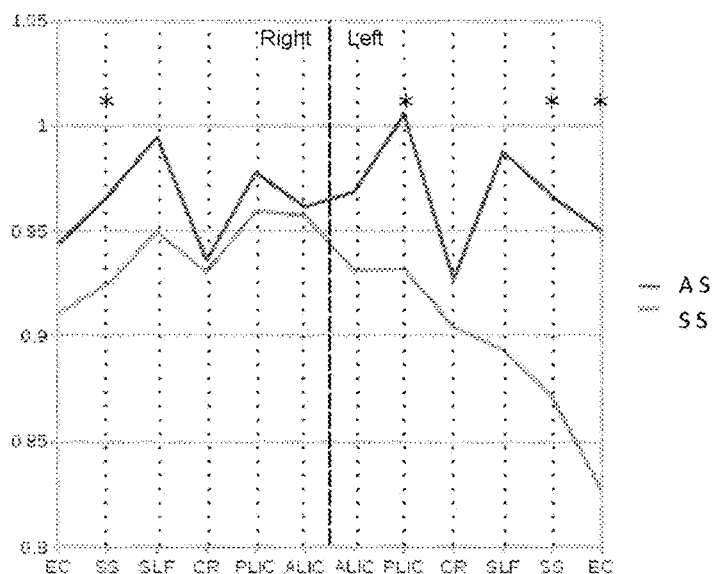

Moreover, 20 regions of interest (ROIs) were defined on the basis of the atlas of 48 regions of white matter constructed from diffusion data from 81 healthy subjects ('ICBM-DTI-81' atlas available in the fsl software). These 20 ROIs were selected by a board of experts (2 neuroradiologists and 1 neuro resuscitator) by taking into account their size, with the original small ROIs eliminated or merged, and their potential diagnostic interest. These 20 regions of interest are represented in FIG. 2, they are indicated by a number from 1 to 20 as a function of the coloring of the image correlated with the scale of shading. These are the middle cerebellar peduncle indicated 1 (ICBM #1), the anterior brain stem indicated 2 (ICBM #2,7,8), the posterior brain stem indicated 3 (ICBM #9,10,11,12,13,14), the genu of the corpus callosium indicated 4 (ICBM #3), the body of the corpus callosium indicated ((ICBM #4), the splenium of the corpus callosium indicated 6 (ICBM #5), the right cerebral peduncle indicated 7(ICBM #15), the left cerebral peduncle indicated 8 (ICBM #16), the right sagittal stratum indicated 9 (ICBM #21,29,31,47), the left sagittal stratum indicated 10 (ICBM #22,30,32,48), the right superior longitudinal fasciculus indicated 11 (ICBM #41), the left superior longitudinal fasciculus indicated 12 (ICBM #42), the anterior limb of the right internal capsule indicated 13 (ICBM #17), the anterior limb of the left internal capsule indicated 14 (ICBM #18), the posterior limb of the right internal capsule indicated 15 (ICBM #19), the posterior limb of the left internal capsule indicated 16 (ICBM #20), the right external capsule indicated 17 (ICBM #33), the left external capsule indicated 18 (ICBM #34), the right corona radiata indicated 19 (ICBM #23,25,27) and the left corona radiata indicated 20 (ICBM #24,26,28).

The 20 regional parameters of FA of each patient are the averages in each ROI of the FA on the skeleton. The 20 parameters of MD, AD and RD were calculated in the same way.

Each patient was therefore characterized by 20 FA parameters (average of the FA on the skeleton in each ROI), 20 AD parameters and 20 RD parameters reflecting the regional integrity of the white matter bundles. These parameters were extracted by masking the FA maps projected onto the skeleton with the mask of the 20 ROIs.

For these parameters to be able to be interpreted relative to a reference normal level, the FA value measured in each ROI was standardized relative to an average value calculated on a population of healthy subjects of the same age, namely at least 10 individuals, from the same machine and from the same MRI acquisition protocols.

For each of the ROIs, the following scores were therefore calculated:

$S\ FA\_n(ROI\#i)=FA(ROI\#0/mean\_controls(FA(ROI\#0)$ $S\ MD\_n(ROI\#i)=MD(ROI\#0/mean\_controls(MDROI\#0)$ $S\ AD\_n(ROI\#i)=AD(ROI\#0/mean\_controls(AD(ROI\#0)$ $S\ RD\_n(ROI\#i)=RD(ROI\#0/mean\_controls(RD(ROI\#0)$ In which "i" corresponds to the number of the region and "mean_controls" corresponds to the normal value for the measured parameter.

Figure 1:
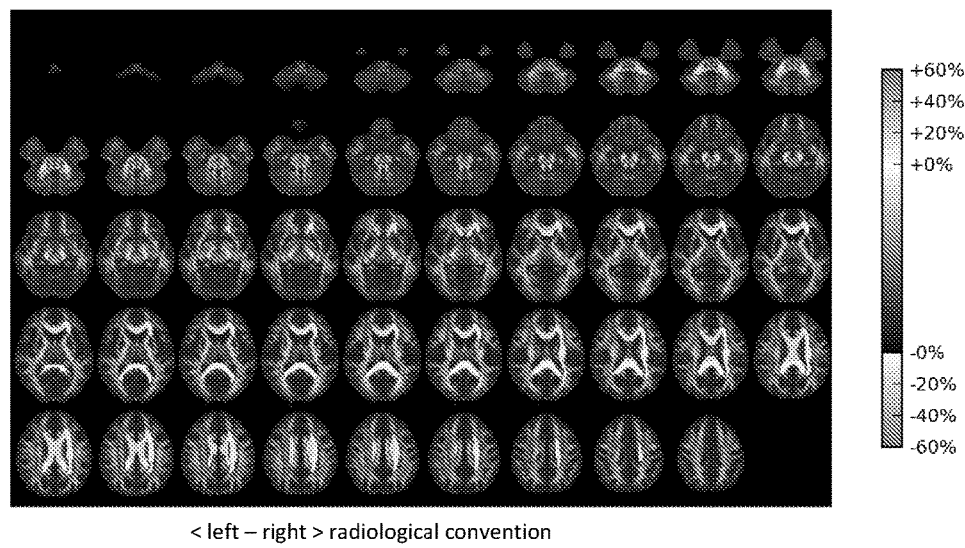
FIG. 1 is an image representing a fractional anisotropy injury map for a patient. In this image, the lightest regions correspond to the injured areas, that is to say those for which the measurement exhibits a significant deviation from the normal.

A brain region exhibiting a significant variation of one of these scores relative to the normal, that is to say plus or minus 2 times the standard deviation of the regional measurements of the control group as indicated in Table 3 below, was considered as injured. The intensity of the injuries is expressed as a percentage variation relative to the average of the measurements of the control group. FIG. 1 represents the percentage as a function of the control values.

The regional standard deviations of the controls (n=85) used to detect the significant variations are presented in Table 3.

TABLE 3

Regional standard deviations

| | Standard deviation FA_n(ROI) as % | Standard deviation MD_n(ROI) as % | Standard deviation AD_n(ROI) as % | Standard deviation RD_n(ROI) as % |
|---|---|---|---|---|
| Middle cerebellar peduncle (ICBM #1) | 4.5 | 4.1 | 3.8 | 6.2 |
| Anterior brain stem (ICBM #2, 7, 8) | 4.4 | 5.3 | 4.6 | 6.9 |
| Posterior brain stem (ICBM #9, 10, 11, 12, 13, 14) | 3.9 | 3.7 | 3.0 | 6.2 |
| Genu of the corpus callosium (ICBM #3) | 4.7 | 4.9 | 3.4 | 11.5 |
| Body of the corpus callosium (ICBM #4) | 8.0 | 6.8 | 3.8 | 13.7 |
| Splenium of the corpus callosium (ICBM #5) | 2.8 | 3.7 | 3.2 | 8.9 |
| Right cerebral peduncle (ICBM #15) | 3.6 | 3.2 | 3.0 | 6.4 |
| Left cerebral peduncle (ICBM #16) | 3.8 | 4.1 | 3.3 | 8.3 |
| Right sagittal stratum (ICBM #21, 29, 31, 47) | 4.7 | 3.4 | 2.9 | 6.0 |
| Left sagittal stratum (ICBM #22, 30, 32, 48) | 4.6 | 3.2 | 2.7 | 6.1 |
| Right superior longitudinal fasciculus (ICBM #41) | 5.2 | 3.1 | 3.1 | 5.1 |
| Left superior longitudinal fasciculus (ICBM #42) | 5.6 | 3.1 | 3.1 | 5.4 |
| Anterior limb of the right internal capsule (ICBM #17) | 4.5 | 3.0 | 3.1 | 5.7 |
| Anterior limb of the left internal capsule (ICBM #18) | 4.3 | 2.7 | 2.6 | 5.4 |
| Posterior limb of the right internal capsule (ICBM #19) | 3.5 | 2.6 | 3.0 | 5.6 |
| Posterior limb of the left internal capsule (ICBM #20) | 3.2 | 2.3 | 3.0 | 4.9 |
| Right external capsule (ICBM #33) | 4.9 | 2.9 | 2.5 | 4.3 |
| Left external capsule (ICBM #34) | 5.2 | 2.2 | 2.2 | 3.9 |
| Right corona radiata (ICBM #23, 25, 27) | 4.9 | 3.3 | 3.0 | 5.1 |
| Left corona radiata (ICBM #24, 26, 28) | 5.0 | 3.0 | 2.7 | 5.1 |

41 patients in a coma after cranial trauma were admitted into the neuro-resuscitation department of Pitié-Salpêtrière hospital. They were included in the study and they met the following criteria:

1) required mechanically assisted respiration for neurological reasons, 2) absence of response to simple commands at the time of signing of the legal consent by the authorized representative, at least seven days after the accident, 3) absence of response to simple commands not linked to the administration of sedatives, 4) general clinical state allowing the patient to be transported, 5) intracranial pressure and cerebral compliance making it possible to maintain the lying-down position for the MRI acquisition without developing intracranial hypertension which would be potentially damaging to the patient.

15 patients who had recovered well were evaluated in the consolidation phase, approximately 2 years after the accident, by the method of the invention comprising the MRI acquisition of diffusion and regional quantification of the injuries. At the same time, the neuropsychological after-effects were assessed by an expert. From this assessment, these 15 patients were ranked in two groups: the normal patients not exhibiting any after-effect (n=10) and those exhibiting after-effects (n=5). Finally, an MRI acquisition was performed on the same machine on 15 control subjects for the diffusion measurements to be standardized.

The details of the MRI acquisitions are as follows: diffusion-weighted sequence, 11 directions, TR/TE=13 000/85.9 ms, diffusion b value=900 s/mm, slice thickness=3 mm without hole, 47 slices, field of view=28×28 cm², matrix 256×256.

20 regional FA values were extracted then standardized relative to the control values, in accordance with the method described previously. The average values of these measurements over the two groups (group without after-effect and group with neurological after-effects) are represented in FIG. 2.

As represented in FIG. 2, the values obtained between the patients with and without after-effects are significantly different. Furthermore, the method of the invention makes it possible to define two distinct groups, one with and the other without after-effects. Thus, the method of the invention advantageously makes it possible to detect an injury, quantify the injury and link this injury with a possible after-effect.

Example 2: Determination of the Algorithm for Tracking a Brain Injury in a Test Subject and Implementation The method of monitoring brain injuries in a patient, in particular the regional quantification of the injuries of the white matter fibers of the brain relies on the measurements of fractional anisotropy (FA) reflecting the overall integrity of the fibers, of axial diffusivity (AD) reflecting the axonal integrity and of radial diffusivity (RD) reflecting the integrity of the myelin sheath.

For this, the aim is to quantify the brain injuries of a patient by following the same method as that described in example 1 at several instants, for example every six months and/or every year.

For a given instant, the quantification of the brain injuries consists of a number of successive steps:

1. An MRI acquisition of the diffusion tensor (DTI) comprising a T2-weighted acquisition (corresponding to a factor b=0) and acquisitions with diffusion-weighted gradients (b~=1000 s/mm²). To apply the model of the tensor, the acquisition with the gradients in at least 6 different directions of the space is necessary.
2. A series of preprocessing of the raw DTI data was performed using the FSL software (http://www.fmrib.ox.ac.uk/fsl/, Smith et al. 2004 [7]).
3. Correction of the distortions induced by the eddy currents (with the "eddy correct" function). This correction consisted in re-registering (rigid re-registration) the diffusion-weighted volumes on the T2-weighted volume as described in Jenkinson et al. 2002 [4].
4. Extraction of the mask of the brain by removing from the volume all the non-brain tissues (with the bet function) as described in Smith 2002 [6].
5. Calculation of the 3 specific values ($\lambda 1$, $\lambda 2$ and $\lambda 3$) of the model of the tensor for each voxel as described in Basser et al. 1996 [2] making it possible to calculate parametric maps of FA, AD and RD (with the dtifit function).

So as to spatially map the parametric maps to the reference maps, that is to say those calculated on healthy control subjects and on groups of patients, to be able to compare them, the latter were projected into a standard space.

For this, the individual FA maps were first of all re-registered by a non-linear re-registration FNIRT ("FMRIB's Non-linear Image Registration Tool") Andersson et al. 2007a [10], Andersson et al. 2007b [11] in a reference space characterized by a reference image calculated on 58 healthy subjects (FMRIB58_FA). To take into account only the maximum FA values along the bundles, these maximum local values were projected onto the skeleton of the main FA bundles according to the TBSS method described in Smith et al. 2006 [8]. This skeleton represents the centers common to the group of the main white matter bundles in the brain. The corresponding values of AD and RD were projected onto the same skeleton according to the same transformation.

Moreover, 20 regions of interest (ROIs) were defined on the basis of the atlas of 48 regions of white matter constructed from diffusion data from 81 healthy subjects (the 'ICBM-DTI-81' atlas available in the fsl software). These 20 ROIs were selected by a board of experts (2 neuroradiologists and 1 neuroresusitator) by taking into account their size, with the small original ROIs eliminated or merged, and their potential diagnostic interest. These 20 regions of interest are represented in FIG. 2, they are indicated by a number from 1 to 20 according to the coloring of the image correlated with the scale of shading. These are the middle cerebellar peduncle indicated 1 (ICBM #1), the anterior brain stem indicated 2 (ICBM #2,7,8), the posterior brain stem indicated 3 (ICBM #9,10,11,12,13,14), the genu of the corpus callosium indicated 4 (ICBM #3), the body of the corpus callosium indicated ((ICBM #4), the splenium of the corpus callosium indicated 6 (ICBM #5), the right cerebral peduncle indicated 7(ICBM #15), the left cerebral peduncle indicated 8 (ICBM #16), the right sagittal stratum indicated 9 (ICBM #21,29,31,47), the left sagittal stratum indicated 10 (ICBM #22,30,32,48), the right superior longitudinal fasciculus indicated 11 (ICBM #41), the left superior longitudinal fasciculus indicated 12 (ICBM #42), the anterior limb of the right internal capsule indicated 13 (ICBM #17), the anterior limb of the left internal capsule indicated 14 (ICBM #18), the posterior limb of the right internal capsule indicated 15 (ICBM #19), the posterior limb of the left internal capsule indicated 16 (ICBM #20), the right external capsule indicated 17 (ICBM #33), the left external capsule indicated 18 (ICBM #34), the right corona radiata indicated 19 (ICBM #23,25,27) and the left corona radiata indicated 20 (ICBM #24,26,28).

The 20 regional FA parameters of each patient are the averages in each ROI of the FA on the skeleton. The 20 parameters of MD, AD and RD were calculated in the same way.

For a given instant, a patient was therefore characterized by 20 FA parameters (average of the FA on the skeleton in each ROI), 20 AD parameters and 20 RD parameters reflecting the regional integrity of the white matter bundles. These parameters were extracted by masking of the FA maps projected onto the skeleton with the mask of the 20 ROIs.

For these parameters to be able to be interpreted relative to a reference normal level, the FA value measured in each ROI was standardized relative to an average value calculated on a population of healthy subjects of the same age, namely at least 10 individuals, from the same machine and from the same MRI acquisition protocols.

For a given instant Tj, for each of the ROIs, the following scores were therefore calculated:

$S\ FA\_n\_Tj(ROI\#i)=FA\_Tj(ROI\#0/mean\_controls(FA(ROI\#0)$ $S\ MD\_n\_Tj(ROI\#i)=MD\_Tj(ROI\#0/mean\_controls(MDROI\#0)$ $S\ AD\_n\_Tj(ROI\#i)=AD\_Tj(ROI\#0/mean\_controls(AD(ROI\#0)$ $S\ RD\_n\_Tj(ROI\#i)=RD\_Tj(ROI\#0/mean\_controls(RD(ROI\#0)$ In which "i" corresponds to the number of the region and "mean_controls" corresponds to the normal value for the measured parameter.

Finally, the trend of the brain injuries between two instants T1 and T2 is determined by calculating the variation $\Delta S_{FA}$, $\Delta S_{DA}$, $\Delta S_{DR}$ according to the following formulae:

$\Delta S_{FA}=S_{FA\_n\_T2}-S_{FA\_n\_T1}$ $\Delta S_{DA}=S_{DA\_n\_T2}-S_{DA\_n\_T1}$ $\Delta S_{DR}=S_{DR\_n\_T2}-S_{DR\_n\_T1}$ A variation of one of these scores by at least 2 times the standard deviation of the regional measurements of the control group as indicated in Table 3 was considered as significant.

A significant negative variation of at least one value $\Delta S_{FA}$, $\Delta S_{DA}$, indicating an aggravation of the injury, a significant positive variation of at least one value $\Delta S_{FA}$, $\Delta S_{DA}$, indicating a recovery, a significant negative variation of $\Delta S_{RD}$ indicating a recovery, a significant positive variation of $\Delta S_{RD}$ indicating an aggravation of the injury.

Take the example of a patient having suffered a severe cranial trauma for whom the trend of the injuries has been tracked between one year after the accident (T1) and three years after the accident (T2). This patient has recovered well and has no after-effects. For this patient, the variations $\Delta S_{FA}$, $\Delta S_{DA}$, $\Delta S_{RD}$ were calculated between T1 and T2 as described previously.

The results of the measurements are represented in Table 4 below:

TABLE 4

Results obtained per region. The significant differences are indicated by *

| Measurements | Time T1 | | | Time T2 | | | Variations (*100) | | |
|---|---|---|---|---|---|---|---|---|---|
| | FA | DA | DR | FA | DA | DR | ΔSFA | ΔSDA | ΔSDR |
| Middle cerebellar peduncle (ICBM #1) | 1.008 | 1.111 | 1.091 | 0.987 | 1.100 | 1.100 | −2.10 | −1.04% | 0.84% |
| Anterior brain stem (ICBM #2, 7, 8) | 0.879 | 1.120 | 1.262 | 0.886 | 1.098 | 1.219 | 0.70 | −2.25 | −4.32 |
| Posterior brain stem (ICBM #9, 10, 11, 12, 13, 14) | 0.988 | 1.020 | 1.060 | 0.971 | 1.033 | 1.092 | −1.70 | 1.29 | 3.23 |
| Genu of the corpus callosium (ICBM #3) | 0.814 | 1.053 | 1.517 | 0.823 | 1.080 | 1.570 | 0.90 | 2.69 | 5.31 |
| Body of the corpus callosium (ICBM #4) | 0.791 | 1.013 | 1.427 | 0.863 | 1.050 | 1.345 | 7.20 | 3.62 | −8.19 |
| Splenium of the corpus callosium (ICBM #5) | 0.931 | 1.030 | 1.253 | 0.950 | 1.034 | 1.185 | 1.90 | 0.37 | −6.79 |
| Right cerebral peduncle (ICBM #15) | 0.947 | 1.012 | 1.115 | 0.935 | 1.011 | 1.142 | −1.20 | −0.15 | 2.75 |
| Left cerebral peduncle (ICBM #16) | 0.964 | 1.026 | 1.092 | 0.943 | 1.007 | 1.118 | −2.10 | −1.85 | 2.66 |
| Right sagittal stratum (ICBM #21, 29, 31, 47) | 1.004 | 1.039 | 1.039 | 1.018 | 1.040 | 1.020 | 1.40 | 0.14 | −1.95 |
| Left sagittal stratum (ICBM #22, 30, 32, 48) | 0.967 | 1.035 | 1.082 | 1.005 | 1.029 | 1.022 | 3.80 | −0.58 | −6.00 |
| Right superior longitudinal fasciculus (ICBM #41) | 1.063 | 1.058 | 0.987 | 1.043 | 1.033 | 0.991 | −2.00 | −2.58 | 0.47 |
| Left superior longitudinal fasciculus (ICBM #42) | 1.040 | 1.042 | 0.983 | 1.099 | 1.060 | 0.944 | 5.90* | 1.84 | −3.92 |
| Anterior limb of the right internal capsule (ICBM #17) | 0.974 | 1.022 | 1.064 | 1.019 | 1.025 | 1.013 | 4.50* | 0.34 | −5.03 |
| Anterior limb of the left internal capsule (ICBM #18) | 0.987 | 1.061 | 1.063 | 0.972 | 1.051 | 1.068 | −1.50 | −0.95 | 0.54 |
| Posterior limb of the right internal capsule (ICBM #19) | 0.994 | 1.049 | 1.050 | 1.019 | 1.009 | 0.967 | 2.50 | −4.01 | −8.33* |
| Posterior limb of the left internal capsule (ICBM #20) | 1.009 | 1.054 | 1.023 | 1.012 | 1.038 | 1.005 | 0.30 | −1.68 | −1.82 |
| Right external capsule (ICBM #33) | 0.942 | 1.032 | 1.082 | 0.950 | 1.019 | 1.072 | 0.80 | −1.31 | −1.06 |
| Left external capsule (ICBM #34) | 0.927 | 1.003 | 1.076 | 0.935 | 0.998 | 1.066 | 0.80 | −0.46 | −0.97 |

TABLE 4-continued

Results obtained per region. The significant differences are indicated by *

| | Time T1 | | | Time T2 | | | Variations (*100) | | |
|---|---|---|---|---|---|---|---|---|---|
| Measurements | FA | DA | DR | FA | DA | DR | ΔSFA | ΔSDA | ΔSDR |
| Right corona radiata (ICBM #23, 25, 27) | 0.949 | 1.112 | 1.169 | 0.934 | 1.134 | 1.232 | −1.50 | 2.18 | 6.32 |
| Left corona radiata (ICBM #24, 26, 28) | 0.893 | 1.047 | 1.149 | 0.924 | 1.047 | 1.122 | 3.10 | 0.00 | −2.78 |

As demonstrated in Table 4 above, the significant variations show a recovery from the injuries of the left superior longitudinal fasciculus ($\Delta S_{FA}$=+5.9%), of the anterior limb of the right internal capsule ($\Delta S_{FA}$=+4.5%) and of the posterior limb of the right internal capsule ($\Delta S_{RD}$=−8.3%).

The method of the present invention therefore makes it possible to track the trend of an injury in a test subject and advantageously makes it possible to identify the regions in which the injury or the injuries have evolved.

Example 3: Determination of the Algorithm for Calculating the Prediction Score for Outcome from the Coma, from the Vegetative State or from the State of Minimal Consciousness for a Patient in Coma after Cranial Trauma Determination of the prediction model by learning from a population of 105 patients.

105 patients in coma, in a vegetative state or a state of minimal consciousness after cranial trauma were admitted into the neuro-resuscitation departments of 10 participating centers. They were included in the study if they met the following criteria:

1) Adults between 18 and 75 years
2) Absence of response to simple commands at the time of signing of the legal consent by the authorized representative, at least seven days and at most 45 days after the accident
3) General clinical state allowing the patient to be transported
4) Cerebral compliance making it possible to maintain the lying-down position for the MRI acquisition without the development of an intracranial hypertension
5) No pathologies of the central nervous system (cerebral vascular accident, brain tumor, neurodegenerative disease) before the accident.

5 to 10 healthy subjects were moreover recruited in each center as control subjects for the diffusion MRI acquisition sequence.

The neurological state 1 year after the accident was assessed for each patient according to the modified GOS scale (Glasgow Outcome Scale). The GOS score 3 is then divided into two categories, the score "3−" corresponding to the state of minimal consciousness, Giacino and Zassler, 1995 [17] and the score "3+" to a severe incapacity. From this scale, the 105 patients were divided up into two groups: the patients with a favorable prognosis (GOS 3+, 4 and 5) and those with an unfavorable prognosis (GOS 1, 2, 3−).

The construction of the supervised classification algorithm corresponding to the step e) of the method was conducted using the LIBSVM library as described in Chang & Lin, 2011 [15]. In this context, each patient was characterized by his or her class (−1 for a patient with unfavorable prognosis and 1 for a patient with favorable prognosis) and by the 80 regional diffusion parameters (SFA_n, SMD_n, SRD_n and SAD_n in the 20 ROIs) calculated according to the method described in the example 1. All of this information was stored in a text file named 'TrainingData.txt'.

Several steps were then carried out:
a) change of scale of the variables between −1 and 1. This step is performed with the svm-scale function of the LIBSVM library by launching the following function: svm-scale -l -1 -u 1 TrainingData.txt
b) choice of Gaussian core for the projection of the data
c) procedure of step-by-step selection of the variables with a combined adjustment of the parameters of the projection core which optimizes the accuracy of the classification (or "classification accuracy"), (algorithm under the python software named "fselect.py tool" available for downloading online at http://www.csie.n-tu.edu.tw/~cjlin/libsvmtools/#feature_selection_tool [17]).

The optimal algorithm F determined by the supervised classification software indicated above ultimately comprises 32 variables. Table 1 below presents the 32 variables.

TABLE 5

| Variables studied | | |
|---|---|---|
| Fractional anisotropy (FA) | Radial diffusion (RD) | Axial diffusion (AD) |
| ROI #1 | ROI #2 | ROI #3 |
| ROI #2 | ROI #3 | ROI #5 |
| ROI #3 | ROI #4 | ROI #10 |
| ROI #4 | ROI #6 | ROI #16 |
| ROI #5 | ROI #7 | ROI #20 |
| ROI #6 | ROI #8 | — |
| ROI #7 | ROI #10 | — |
| ROI #8 | ROI #15 | — |
| ROI #10 | ROI #16 | — |
| ROI #13 | ROI #18 | — |
| ROI #14 | ROI #19 | — |
| ROI #15 | ROI #20 | — |
| ROI #16 | — | — |
| ROI #18 | — | — |

The list of the variable numbers is presented below.

TABLE 6

| Variable number according to the variable | |
|---|---|
| Variable name | Variable number |
| FA - ROI #1 | 1 |
| FA - ROI #2 | 2 |
| FA - ROI #3 | 3 |
| FA - ROI #4 | 4 |
| FA - ROI #5 | 5 |
| FA - ROI #6 | 6 |
| FA - ROI #7 | 7 |
| FA - ROI #8 | 8 |

TABLE 6-continued

Variable number according to the variable

| Variable name | Variable number |
|---|---|
| FA - ROI #9 | 9 |
| FA - ROI #10 | 10 |
| FA - ROI #13 | 13 |
| FA - ROI #14 | 14 |
| FA - ROI #15 | 15 |
| FA - ROI #16 | 16 |
| FA - ROI #18 | 18 |
| AD - ROI #3 | 83 |
| AD - ROI #5 | 85 |
| AD - ROI #10 | 90 |
| AD - ROI #16 | 96 |
| AD - ROI #20 | 100 |
| RD - ROI #2 | 122 |
| RD - ROI #3 | 123 |
| RD - ROI #4 | 124 |
| RD - ROI #6 | 126 |
| RD - ROI #7 | 127 |
| RD - ROI #8 | 128 |
| RD - ROI #10 | 130 |
| RD - ROI #15 | 135 |
| RD - ROI #16 | 136 |
| RD - ROI #18 | 138 |
| RD - ROI #19 | 139 |
| RD - ROI #20 | 140 |

FIG. 4 presents the results obtained for each of the 105 patients. In this figure, each measurement range is referenced by a number and the results indicated as a function of the variable number in bold defined in Table 6.

The algorithm F comprising the selected optimal parameters and the selected support vectors were saved in a text file 'predictModel.txt'.

The application of the algorithm F makes it possible to calculate an sDTI score or predictive value for a given patient.

Figure 3:
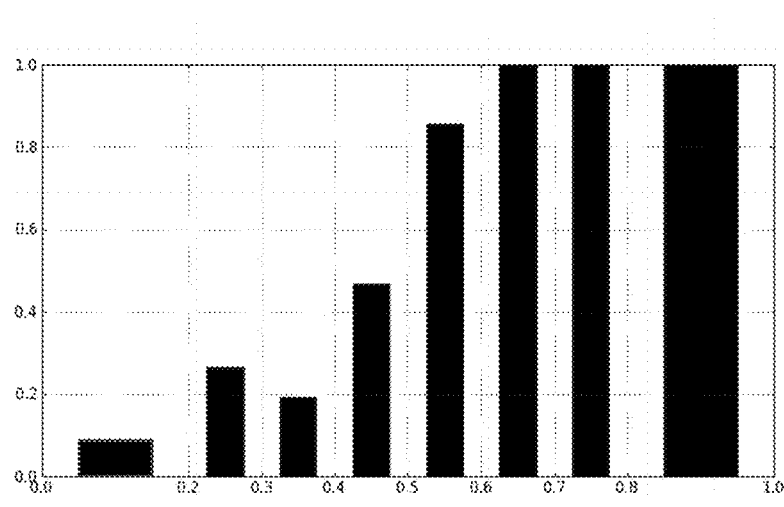
FIG. 3 is a bar chart representing the probability of non-outcome from coma, from the vegetative state or from the state of minimal consciousness as a function of the prediction value. In this chart, a value equal to 1 indicating a certainty of non-outcome from coma, from the vegetative state or from the state of minimal consciousness, a value equal to 0 indicating a certainty of outcome from coma, from the vegetative state or from the state of minimal consciousness.

The efficiency of this classification algorithm was determined by cross-validation, an sDTI score was calculated for each of the 105 patients. From these scores, we determined, for each score interval [0, 0.2], [0, 2, 0.3], [0.3, 0.4], [0.4, 0.5], [0.5, 0.6], [0.6, 0.7], [0.7, 0.8], [0.8, 1], the ratio of the number of patients with an unfavorable prognosis to the total number of patients having a score within said interval. The results represented in FIG. 3 made it possible to define three prediction bands.

In this example, a positive range of sDTI scores or of prediction values lies between 0 and 0.2 and corresponds to a favorable prognosis of outcome from coma, from the vegetative state or from the state of minimal consciousness, a negative range of sDTI scores or of prediction values lies between 0.6 and 1 and corresponds to an unfavorable prognosis of outcome from coma, from the vegetative state or from the state of minimal consciousness, and an intermediate range of sDTI scores or of prediction values lying between 0.2 and 0.6 corresponding to an indecisive prognosis. Following this determination, the method of the invention was implemented for two given patients.

For a new given patient having a brain injury and being in coma for whom the probability of eventual outcome is unknown, the parameters/regional values of SFA, SAD and SRD were extracted from the 20 ROIs according to the method described in the example 1. The calculation of the prediction score for outcome from coma sDTI were then carried out according to the following procedure:

1. Creation of the Parameter File for the New Patient

The following 32 regional parameters SFA_n, SAD_n and SRD_n were extracted and saved in a text file 'patientData.txt' in the following format:

"1 numVar1:Value1 numVar2:Value2 . . . . numVar32:Value32"

where "numVarn" is the number of the variable as defined in the abovementioned Table 6 and Value n is the value of the corresponding parameter.

The calculation of the score or prediction value sDTI from the algorithm F and measurements of the patient were performed with the svm-predict function of the LIBSVM library with the following command:

svm-predict -b 1 patientData.txt predictModel.txt sDTI.txt which made it possible to obtain a text file entitled 'sDTI.txt' comprising the following information:

"Class predicted by the model Probability of belonging to the predicted class" where the Class C predicted by the model can take the values 1 (favorable prognosis) or (−1 unfavorable prognosis) and the Probability P of belonging to the predicted class can take values between 0.5 and 1.

The prediction score or prediction value sDTI corresponding to the probability of unfavorable prognosis is:

$sDTI = P$ if $C = -1$ $1 - P$ if $C = 1$

Thus, for this given patient, it is possible to calculate the probability of an unfavorable prognosis thus making it possible to determine a prediction of outcome from coma, from the vegetative state or from the state of minimal consciousness of said test subject.

The method was implemented on two patients in a coma after a severe cranial trauma, in the present example named patient1 and patient2.

For these two patients, the 32 regional parameters SFA_n, SAD_n and SRD_n were extracted and saved in a text file 'patientData_patient1.txt' and 'patientData_patient2.txt' according to the procedure described previously.

Table 7 below comprises the measurements obtained for each patient classified as a function of the variable number as indicated in Table 6.

TABLE 7

Value of the 32 variables for the patients 1 and 2

| | Variable number | | | | | | | | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 13 | 14 | 15 | 16 | 18 | 83 | 85 | 90 |
| Patient 1 | 0.954 | 0.971 | 0.982 | 0.864 | 1.201 | 1.045 | 0.943 | 1.009 | 0.956 | 0.981 | 0.789 | 0.948 | 0.945 | 1.033 | 1.039 | 0.95 | 1.012 | 1.006 |
| Patient 2 | 0.739 | 0.779 | 0.659 | 0.546 | 0.488 | 0.63 | 0.662 | 0.612 | 0.596 | 0.565 | 0.489 | 0.444 | 0.702 | 0.666 | 0.536 | 0.967 | 0.971 | 1.094 |

TABLE 7-continued

Value of the 32 variables for the patients 1 and 2

| | Variable number | | | | | | | | | | | |
|---|---|---|---|---|---|---|---|---|---|---|---|---|
| | 96 | 100 | 122 | 123 | 124 | 126 | 127 | 128 | 130 | 135 | 136 | 138 | 140 |
| Patient 1 | 0.951 | 1.02 | 0.964 | 0.966 | 1.307 | 0.89 | 1.049 | 1.019 | 1.04 | 1.04 | 0.91 | 0.991 | 1.037 |
| Patient 2 | 0.974 | 1.073 | 1.606 | 1.372 | 1.966 | 1.612 | 1.493 | 1.657 | 1.721 | 1.435 | 1.582 | 1.567 | 1.494 |

The application of the method for calculating the prediction score sDTI from the algorithm F made it possible to determine a prediction score for each patient via the application of the following command: svm-predict-b 1 patientData_patient1.txt predictModel.txt sDTI_patient1.txt svm-predict-b 1 patientData_patient2.txt predictModel.txt sDTI_patient2.txt The scores (sDTI) for each patient were then calculated and were respectively equal to 0.087 for the patient 1 and 0.837 for the patient 2. These scores were generated in a text file respectively named: sDTI_patient1.txt and sDTI_patient2.txt. By comparison of the scores or predictive values to the prediction ranges defined previously, the patient 1 with a predictive value (sDTI) of 0.087 is within the range [0,0.2] corresponding to a favorable prognosis of outcome from coma and 0.837 is in the range [0.6,1] corresponding to an unfavorable prognosis of outcome from coma.

The patient 2 finally died in resuscitation and the patient 1 woke up and was assessed GOS 4 one year after the accident, corresponding to moderate after-effects without dependency.

As demonstrated in this example, the method of the invention makes it possible to reliably determine the prediction of the outcome or not from coma of a patient having suffered a brain injury.

Example 4: Determination of a Formula for Calculating a Prediction Score of the Outcome from Coma, from the Vegetative State or from the State of Minimal Consciousness for a Patient in a Coma after Cardiac Arrest From a database of patients in a coma which were included in the study if they met the following criteria:
1) Adults between 18 and 75 years
2) Absence of response to simple commands at the time of signing of the legal consent by the authorized representative, at least seven days and at most 45 days after the accident
3) General clinical state allowing the patient to be transported
4) Cerebral compliance making it possible to maintain the lying-down position for the MRI acquisition without developing an intracranial hypertension
5) No pathologies of the central nervous system (cerebral vascular accident, brain tumor, neurodegenerative disease) before the cardiac arrest.

Method

The 100 patients were separated into two groups according to their neurological state 1 year after their accident, determined according to the extended Glasgow scale (GOSE) (GOSE=[1,3] for the unfavorable prognoses, GOSE=[4-8] for the favorable prognoses). Each patient was characterized by a set of variables X_i comprising the regional measurements of FA, in the 20 regions of interest defined above, the age and by the time period in days delta between the accident and the MRI examination, the optimal parameters beta_i such as the score were calculated as follows:

$$scoreDTI = \frac{1}{1 + e^{beta_0 + \sum_i beta_i \cdot X_i}} \quad \text{(formula 1)}$$

Two alternative formulae were calculated, one assigning a (a priori) non-zero weight beta_i to each variable X_i (complete DTI score), the other assigning zero beta_i weights to the least discriminating variables X_i (compact DTI score). In both cases, the optimal parameters beta_i were determined by cross validation according to the method described in Picard R., Cook D. (1984): Cross-Validation of Regression Models. Journal of the American Statistical Association 79 (387): 575-583. [18].

The DTI score was assessed on the patients in a coma after a cardiac arrest, after a severe cranial trauma, and a meningeal hemorrhage.

Table 8 below summarizes, for each region of interest, the values of the beta_i coefficients as a function of the regions of interest when the fractional anisotropy is measured in the abovementioned 20 regions for the patients in a coma after cardiac arrest.

TABLE 8

Parameters of the complete DTI score for the patients in a coma after cardiac arrest

| Predictors X_i | Model parameters beta_i |
|---|---|
| Intercept (beta_0) | −24.5214885485 |
| Middle cerebellar peduncle (ICBM #1) | 0.0 |
| Anterior brain stem (ICBM #2, 7, 8) | 0.0 |
| Posterior brain stem (ICBM #9, 10, 11, 12, 13, 14) | 0.0 |
| Genu of the corpus callosium (ICBM #3) | 6.87535790908 |
| Body of the corpus callosium (ICBM #4) | 4.06938927662 |
| Splenium of the corpus callosium (ICBM #5) | 11.855208917 |
| Right cerebral peduncle (ICBM #15) | −4.85084571328 |
| Left cerebral peduncle (ICBM #16) | 2.15989083485 |
| Right sagittal stratum (ICBM #21, 29, 31, 47) | 4.2325734777 |
| Left sagittal stratum (ICBM #22, 30, 32, 48) | −3.34425242349 |
| Right superior longitudinal fasciculus (ICBM #41) | −6.85002870016 |
| Left superior longitudinal fasciculus (ICBM #42) | −4.99481835312 |
| Anterior limb of the right internal capsule (ICBM #17) | 2.0487983025 |
| Anterior limb of the left internal capsule (ICBM #18) | 7.22561663595 |

TABLE 8-continued

Parameters of the complete DTI score for the
patients in a coma after cardiac arrest

| Predictors X_i | Model parameters beta_i |
|---|---|
| Posterior limb of the right internal capsule (ICBM #19) | 1.8759969088 |
| Posterior limb of the left internal capsule (ICBM #20) | −0.232791690832 |
| Right external capsule (ICBM #33) | 6.39302863473 |
| Left external capsule (ICBM #34) | 0.0222995384139 |
| Right corona radiata (ICBM #23, 25, 27) | −0.0594003555767 |
| Left corona radiata (ICBM #24, 26, 28) | 0.145161164427 |

Figure 5:
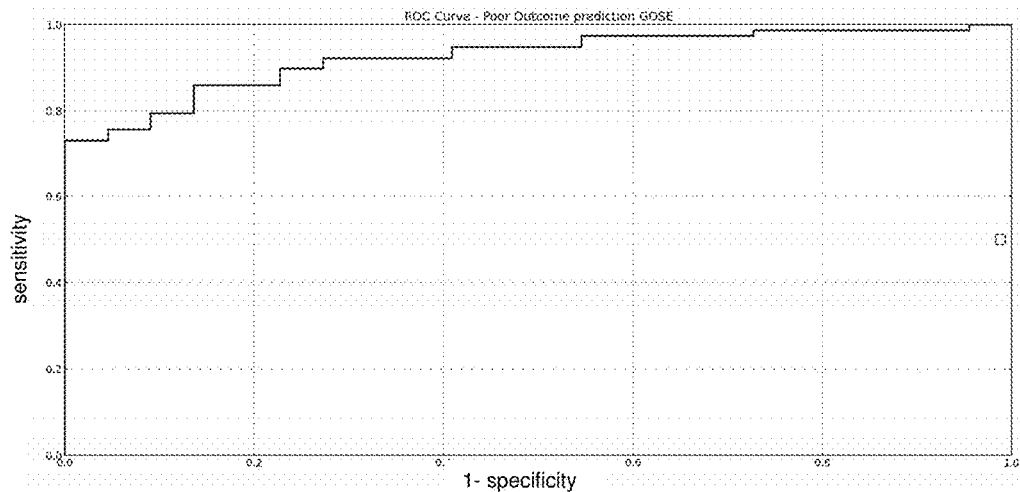
FIG. 5 represents an ROC curve for the prediction of the unfavorable prognosis for patients after cardiac arrest with the DTI score calculated from the 20 regions, the y axis represents the sensitivity, the x axis 1-specificity.

FIG. 5 represents an ROC curve obtained according to the method described for example in [19] for the prediction of the unfavorable prognosis of the patients after cardiac arrest, the y axis represents the sensitivity, the x axis 1-specificity. As demonstrated in this figure, the sensitivity of prediction of the unfavorable prognosis is 73% for a specificity of 100%.

Figure 6:
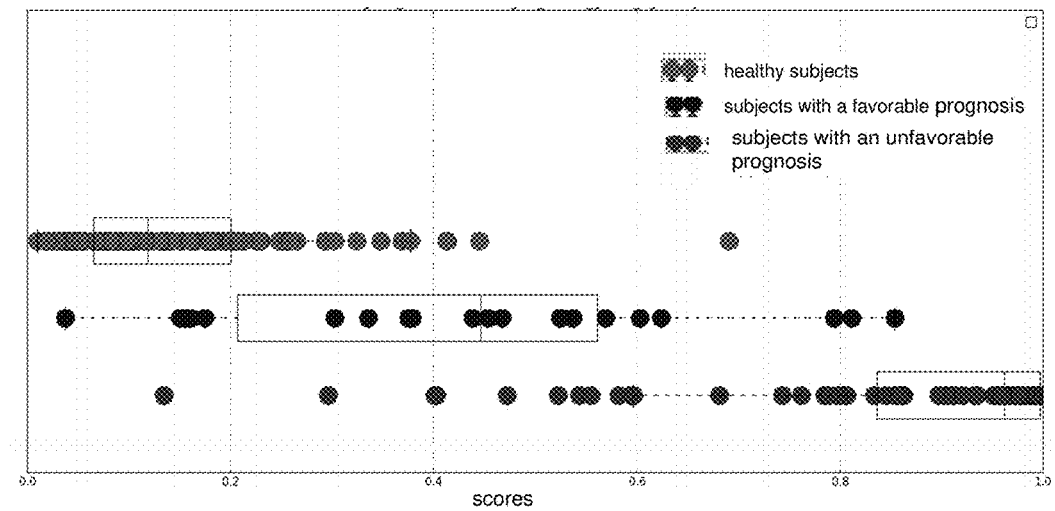
FIG. 6 represents a distribution of the DTI score calculated from the 20 regions for the cardiac arrest patients with favorable prognosis (points in the middle/middle line) and unfavorable prognosis (bottom points, bottom line) and the group of 105 healthy subjects (upper points, top line). The compact DTI score for the patients is obtained by cross-validation ("leave-one-out"), that for the controls was obtained by direct calculation according to the formula 1 and the parameters of Table 8.

FIG. 6 represents the DTI score values obtained as a function of the patients classified according to the GOS score.

Thus, as represented in FIG. 6, a DTI score lying between 0.83 and 1 signifies an unfavorable prediction of outcome from coma.

Table 9 below summarizes, for each region of interest, the values of the $beta_i$ coefficients as a function of the regions of interest when the fractional anisotropy is only measured in the abovementioned 5 regions independently of the age and of the time after the cardiac arrest. Thus, the beta_i coefficients are mentioned as equal to zero in Table 9 below when the measurement of the FA in the region or regions of interest has not been performed.

TABLE 9

Parameters of the complete DTI score for the
patients in a coma after cardiac arrest

| Predictors X_i | Model parameters beta_i |
|---|---|
| Intercept (beta_0) | −20.7785254295 |
| Age | 0.0 |
| Delta | 0.0 |
| Middle cerebellar peduncle (ICBM #1) | 0.0 |
| Anterior brain stem (ICBM #2, 7, 8) | 0.0 |
| Posterior brain stem (ICBM #9, 10, 11, 12, 13, 14) | 0.0 |
| Genu of the corpus callosium (ICBM #3) | 0.0 |
| Body of the corpus callosium (ICBM #4) | 0.0 |
| Splenium of the corpus callosium (ICBM #5) | 0.0 |
| Right cerebral peduncle (ICBM #15) | 0.0 |
| Left cerebral peduncle (ICBM #16) | 1.87189152758 |
| Right sagittal stratum (ICBM #21, 29, 31, 47) | 0.0 |
| Left sagittal stratum (ICBM #22, 30, 32, 48) | 0.0 |
| Right superior longitudinal fasciculus (ICBM #41) | 0.0 |
| Left superior longitudinal fasciculus (ICBM #42) | 0.0 |
| Anterior limb of the right internal capsule (ICBM #17) | 1.19502993841 |
| Anterior limb of the left internal capsule (ICBM #18) | 1.7329368258 |

TABLE 9-continued

Parameters of the complete DTI score for the
patients in a coma after cardiac arrest

| Predictors X_i | Model parameters beta_i |
|---|---|
| Posterior limb of the right internal capsule (ICBM #19) | 0.0 |
| Posterior limb of the left internal capsule (ICBM #20) | 0.0 |
| Right external capsule (ICBM #33) | 10.1577820013 |
| Left external capsule (ICBM #34) | 0.0 |
| Right corona radiata (ICBM #23, 25, 27) | 0.0 |
| Left corona radiata (ICBM #24, 26, 28) | 7.3919471341 |

Figure 7:
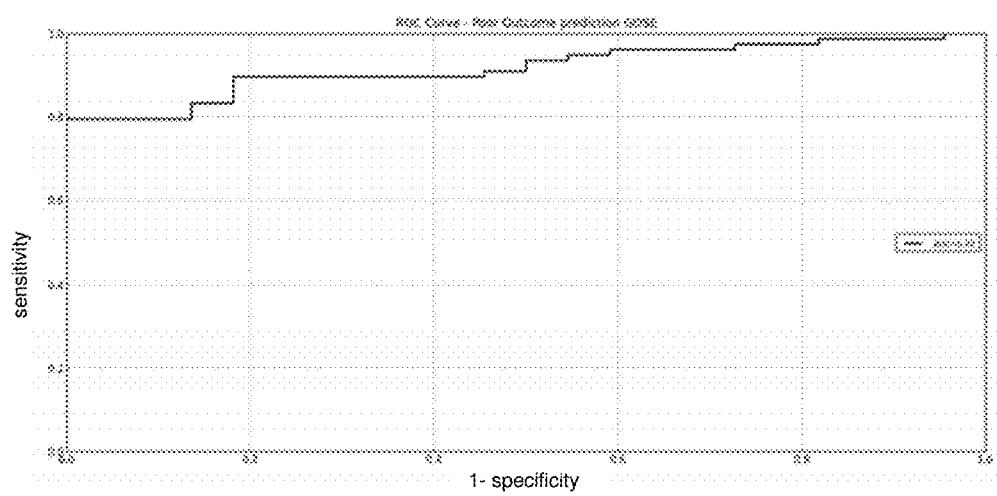
FIG. 7 represents an ROC curve for the prediction of the unfavorable prognosis for patients after cardiac arrest, the y axis represents the sensitivity, the x axis 1-specificity. The DTI score calculated from the five selected regions (the left cerebral peduncle (ICBM #16), the anterior limb of the right internal capsule (ICBM #17), the anterior limb of the left internal capsule (ICBM #18), the right external capsule (ICBM #33), the left corona radiata (ICBM #24,26,28)) for the patients was obtained by cross validation ("leave-one-out").

FIG. 7 represents an ROC curve obtained according to the method described for example in Fawcett T. (2006): An introduction to ROC analysis. Pattern Recognition Letters, 27, 861-874 [19] for the prediction of the unfavorable prognosis of the patients after cardiac arrest, the y axis represents the sensitivity, the x axis 1-specificity. As demonstrated in this figure, the sensitivity of prediction of the unfavorable prognosis is 80% for a specificity of 100%.

Figure 8:
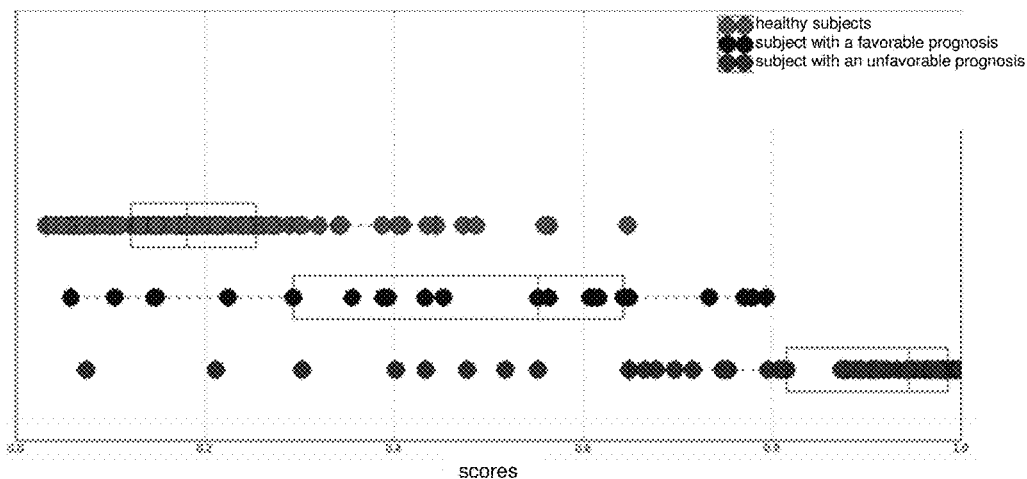
FIG. 8 represents the distribution of the DTI score calculated from the five selected regions (the left cerebral peduncle (ICBM #16), the anterior limb of the right internal capsule (ICBM #17), the anterior limb of the left internal capsule (ICBM #18), the right external capsule (ICBM #33), the left corona radiata (ICBM #24,26,28)) for the cardiac arrest patients with favorable prognosis (intermediate points, middle line) and unfavorable prognosis (bottom points, bottom line) and the group of 105 healthy subjects (top points, top line).

FIG. 8 represents the DTI score values obtained as a function of the patients classified according to the GOS score.

Thus, as represented in FIG. 8, a DTI score lying between 0.8 and 1 signifies an unfavorable prediction of outcome from coma.

Surprisingly, the inventors have thus demonstrated that the DTI score determined in this way makes it possible to predict the outcome from coma after a cardiac arrest with a sensitivity and a specificity of 80% and 100% respectively.

LIST OF REFERENCES

1. [Basser et al. 1994] P. J. Basser, J. Mattiello, D. LeBihan, *MR diffusion tensor spectroscopy and imaging*. Biophysical Journal, 66(1):259-267, 1994.
2. [Basser and Pierpaoli 1996] P. J. Basser and C. Pierpaoli, *Microstructural and Physiological Features of Tissues Elucidated by Quantitative-Diffusion-Tensor MRI*. Journal of Magnetic Resonance, 111(3):209-219, 1996.
3. [Jenkinson and Smith 2001] M. Jenkinson and S. M. Smith, *A global optimisation method for robust affine registration of brain images*. Medical Image Analysis, 5(2):143-156, 2001.
4. [Jenkinson et al. 2002] M. Jenkinson, P. R. Bannister, J. M. Brady, and S. M. Smith, *Improved optimisation for the robust and accurate linear registration and motion correction of brain images*. NeuroImage, 17(2):825-841, 2002.
5. [Lescot et al. 2008] T. Lescot, L. Abdennour, A.-L. Boch, L. Puybasset, *Treatment of intracranialhypertension*. Curr Opin Crit Care, 14:129-134, 2008.
6. [Smith 2002] S. M. Smith, Fast robust automated brain extraction. Human Brain Mapping, 17(3):143-155, 2002.
7. [Smith et al. 2004] S. M. Smith, M. Jenkinson, M. W. Woolrich, C. F. Beckmann, T. E. J. Behrens, H. Johansen-Berg, P. R. Bannister, M. De Luca, I. Drobnjak, D. E. Flitney, R. Niazy, J. Saunders, J. Vickers, Y. Zhang, N. De Stefano, J. M. Brady, and P. M. Matthews, *Advances in functional and structural MR image analysis and implementation as FSL*. NeuroImage, 23(S1):208-219, 2004.
8. [Smith et al. 2006] S. M. Smith, M. Jenkinson, H. Johansen-Berg, D. Rueckert, T. E. Nichols, C. E. Mackay, K. E. Watkins, O. Ciccarelli, M. Z. Cader, P. M. Matthews, and T. E. J. Behrens, Tract-based spatial statistics: *Voxelwise analysis of multi-subject diffusion data*. NeuroImage, 31:1487-1505, 2006.
9. [Mori et al. 2005] S. Mori, S. Wakana, L. M. Nagae-Poetscher, and P. C. M. van Zijl. *MRI Atlas of Human White Matter*. Elsevier, Amsterdam, The Netherlands (2005)
10. [Andersson 2007a] J. L. R. Andersson, M. Jenkinson and S. Smith. *Non-linear optimisation*. FMRIB technical report TR07JA1 from www.fmrib.ox.ac.uk/analysis/techrep
11. [Andersson 2007b] J. L. R. Andersson, M. Jenkinson and S. Smith. *Non-linear registration, aka Spatial normalisation*. FMRIB technical report TR07JA2 from www.fmrib.ox.ac.uk/analysis/techrep
12. [Cox et al. 2004] Robert W. Cox, John Ashburner, Hester Breman, Kate Fissell, Christian Haselgrove, Colin J. Holmes, Jack L. Lancaster, David E. Rex, Stephen M. Smith, Jeffrey B. Woodward, Stephen C. Strother (2004). A (Sort of) New Image Data Format Standard: NifTI-1. NeuroImage, Vol. 22 (2004)
13. [Rorden & Brett, 2000] Rorden, C., Brett, M. (2000). Stereotaxic display of brain lesions. Behavioural Neurology, 12, 191-200.
14. [Chang & Lin, 2011] Chih-Chung Chang and Chih-Jen Lin, LIBSVM: a library for support vector machines. ACM Transactions on Intelligent Systems and Technology, 2:27:1-27:27, 2011. Software available at http://www.csie.ntu.edu.tw/~cjlin/libsvm
15. [Chen & Lin, 2005] Y.-W. Chen and C.-J. Lin, Combining SVMs with various feature selection strategies. Chapter of the book "Feature Extraction: Foundations and Applications (Studies in Fuzziness and Soft Computing)" By Isabelle Guyon, Steve Gunn, Masoud Nikravesh, Lotfi A. Zadeh. Publisher: Springer I ISBN: 3540354875 edition 2006
16. http://www.csie.ntu.edu.tw/~cjlin/libsvmtools/#feature_selectiontool
17. Giacino J. T., Zasler N. D. (1995): Outcome after severe traumatic brain injury: coma, the vegetative state, and the minimally responsive state. J Head Trauma Rehabil 10:40-56.
18. Picard R., Cook D. (1984): Cross-Validation of Regression Models. Journal of the American Statistical Association 79 (387): 575-583.
19. Fawcett T. (2006): An introduction to ROC analysis. Pattern Recognition Letters, 27,861-874.

The invention claimed is:

1. An ex-vivo method of detecting and/or quantifying brain injuries of a test subject comprising:
 a) measuring the fractional anisotropy $FA_1$ in at least one first region of the brain on an image obtained by magnetic resonance imaging (MRI) of the brain of said test subject,
 b) measuring the axial diffusivity $DA_1$ in at least one second region of the brain on an image obtained by magnetic resonance imaging (MRI) of the brain of said test subject,
 c) measuring the radial diffusivity $DR_1$ in at least one third region of the brain on an image obtained by magnetic resonance imaging (MRI) of the brain of said test subject,
 d) determining the ratios SFA, SDA, and SDR as defined below by comparison of the measured values $FA_1$, $DA_1$, $DR_1$ to normal regional values from a reference group of healthy subjects of fractional anisotropy $FA_n$, of axial diffusivity $DA_n$ and of radial diffusivity $RD_n$, for said regions according to the following formulae:

$$SFA=(FA_1/FA_n)$$

$$SDA=(DA_1/DA_n)$$

$$SRD=(DR_1/DR_n)$$

d') determining that said region of the brain of said test subject is injured if the value of SFA, SDA, and/or SDR is greater than or less than 1 plus or minus two times the standard deviation of the regional measurements from the reference group of healthy subjects respectively of the reference fractional anisotropy, axial diffusivity, radial diffusivity in said region of interest.

2. The method as claimed in claim 1, wherein the method further comprises a step f) determining the intensity of the injuries by measurement of the variation against the average of the reference values.

3. The method as claimed in claim 1, wherein the method further comprises a step f) determining the intensity of the injuries by regions ($I_{les}$) according to the following formula:

$$I_{les}=(((FA_1-FA_{ref})\times 100)/FA_{ref})+(((DA_1-DA_{ref})\times 100)/DA_{ref})+(((DR_1-DR_{ref})\times 100)/DR_{ref}).$$

4. The method as claimed in claim 1, wherein the reference regional values are of the reference average values measured in at least one identical or different reference patient.

5. The method as claimed in claim 1, wherein the measurements of fractional anisotropy, axial diffusivity, radial diffusivity are performed in at least one of the regions of the brain selected from the middle cerebellar peduncle (ICBM #1), the anterior brain stem (ICBM #2,7,8), the posterior brain stem (ICBM #9,10,11,12,13,14), the genu of the corpus callosium (ICBM #3), the body of the corpus callosium (ICBM #4), the splenium of the corpus callosium (ICBM #5), the right cerebral peduncle (ICBM #15), the left cerebral peduncle (ICBM #16), the right sagittal stratum (ICBM #21,29,31,47), the left sagittal stratum (ICBM #22, 30,32,48), the right superior longitudinal fasciculus (ICBM #41), the left superior longitudinal fasciculus (ICBM #42), the anterior limb of the right internal capsule (ICBM #17), the anterior limb of the left internal capsule (ICBM #18), the posterior limb of the right internal capsule (ICBM #19), the posterior limb of the left internal capsule (ICBM #20), the right external capsule (ICBM #33), the left external capsule (ICBM #34), the right corona radiata (ICBM #23,25,27), the left corona radiata (ICBM #24,26,28).

6. The method as claimed in claim 1, wherein the measurements of fractional anisotropy, axial diffusivity, radial diffusivity are performed in all the following regions of the brain: the middle cerebellar peduncle (ICBM #1), the anterior brain stem (ICBM #2,7,8), the posterior brain stem (ICBM #9,10,11,12,13,14), the genu of the corpus callosium (ICBM #3), the body of the corpus callosium (ICBM #4), the splenium of the corpus callosium (ICBM #5), the right cerebral peduncle (ICBM #15), the left cerebral peduncle (ICBM #16), the right sagittal stratum (ICBM #21,29,31, 47), the left sagittal stratum (ICBM #22,30,32,48), the right superior longitudinal fasciculus (ICBM #41), the left superior longitudinal fasciculus (ICBM #42), the anterior limb of the right internal capsule (ICBM #17), the anterior limb of the left internal capsule (ICBM #18), the posterior limb of the right internal capsule (ICBM #19), the posterior limb of the left internal capsule (ICBM #20), the right external capsule (ICBM #33), the left external capsule (ICBM #34), the right corona radiata (ICBM #23,25,27), the left corona radiata (ICBM #24,26,28).

7. The method as claimed in claim 1, wherein the measurements of the fractional anisotropy, axial diffusivity and radial diffusivity are performed on an MRI image taken on a test subject having suffered a cranial and/or brain trauma.

8. The method as claimed in claim 1, wherein the measurements of the fractional anisotropy, axial diffusivity and radial diffusivity are performed on an MRI image taken on a test subject having suffered a brain injury, a meningeal hemorrhage, an aneurismal meningeal hemorrhage, an ischemic attack, an intraparenchymal hemorrhagic attack, a cerebral anoxia.

9. An ex-vivo method of monitoring the trend of a brain injury in a test subject comprising the following steps at a time $t_0$ and at a time $t_1$:
   a) measuring the fractional anisotropy $FA_1$ at $t_0$ and $FA_2$ at $t_1$ in at least one first region of the brain on an image obtained by magnetic resonance imaging (MRI) of the brain of a test subject,
   b) measuring the axial diffusivity $DA_1$ at $t_0$ and $DA_2$ at $t_1$ in at least one second region of the brain on an image obtained by magnetic resonance imaging (MRI) of the brain of said test subject,
   c) measuring the radial diffusivity $DR_1$ at $t_0$ and $DR_2$ at $t_1$ in at least one third region of the brain on an image obtained by magnetic resonance imaging (MRI) of the brain of said test subject,
   d) determining the ratios $S_{FA}1$, $S_{DA}1$, $S_{RD}1$, $S_{FA}2$, $S_{DA}2$, and $S_{RD}2$ as defined below by comparison of the measured values $FA_1$, $DA_1$, $DR_1$, $FA_2$, $DA_2$, $DR_2$ against normal regional values of fractional anisotropy $FA_n$, of axial diffusivity $DA_n$ and of radial diffusivity $DR_n$, for said regions according to the following formulae:

$S_{FA}1=(FA_1/FA_n)$ $S_{DA}1=(DA_1/DA_n)$ $S_{DR}1=(DR_1/DR_n)$ $S_{FA}2=(FA_2/FA_n)$ $S_{DA}2=(DA_2/DA_n)$ $S_{DR}2=(DR_2/DR_n)$ e) determination of the variation $\Delta S_{FA}$, $\Delta S_{DA}$, $\Delta S_{DR}$ according to the following formulae:

$\Delta S_{FA}=S_{FA}2-S_{FA}1$ $\Delta S_{DA}=S_{DA}2-S_{DA}1$ $\Delta S_{DR}=S_{DR}2-S_{DR}1$ e') determining that an aggravation of the injury has occurred if there is a negative variation of at least one value $\Delta S_{FA}$, $\Delta S_{DA}$, e'') determining that a recovery of the injury has occurred if there is a positive variation of at least one value $\Delta S_{FA}$, $\Delta S_{DA}$,
   e''') determining that a recovery of the injury has occurred if there is a negative variation of $\Delta S_{DR}$, and
   e'''') determining that an aggravation of the injury has occurred if there is a positive variation of $\Delta S_{DR}$.

10. The method as claimed in claim 9, wherein the reference patient is identical to the test subject.

* * * * *